United States Patent
Hashimoto et al.

(10) Patent No.: US 7,491,311 B2
(45) Date of Patent: * Feb. 17, 2009

(54) NUCLEIC ACID DETECTION SENSOR

(75) Inventors: Koji Hashimoto, Sagamihara (JP);
Hirohisa Miyamoto, Kamakura (JP);
Kazuhiro Itsumi, Kawasaki (JP);
Kouhei Suzuki, Yokohama (JP)

(73) Assignee: Kabushiki Kaisha Toshiba, Tokyo (JP)

(*) Notice: Subject to any disclaimer, the term of this patent is extended or adjusted under 35 U.S.C. 154(b) by 799 days.

This patent is subject to a terminal disclaimer.

(21) Appl. No.: 10/957,700

(22) Filed: Oct. 5, 2004

(65) Prior Publication Data

US 2005/0048558 A1 Mar. 3, 2005

Related U.S. Application Data

(62) Division of application No. 09/961,249, filed on Sep. 25, 2001, now Pat. No. 6,818,109.

(30) Foreign Application Priority Data

Sep. 29, 2000 (JP) .............................. 2000-301516

(51) Int. Cl.
*G01N 27/327* (2006.01)

(52) U.S. Cl. .................................. 205/777.5; 205/792
(58) Field of Classification Search ................ 204/403.01–403.15; 205/777.5, 778, 792
See application file for complete search history.

(56) References Cited

U.S. PATENT DOCUMENTS

| 5,776,672 | A | 7/1998 | Hashimoto et al. |
| 5,936,686 | A | 8/1999 | Okumura et al. |
| 5,945,286 | A | 8/1999 | Krihak et al. |
| 5,965,452 | A | 10/1999 | Kovacs |
| 5,972,692 | A | 10/1999 | Hashimoto et al. |
| 6,670,131 | B2 | 12/2003 | Hashimoto |
| 6,818,109 | B2 * | 11/2004 | Hashimoto et al. ..... 204/403.04 |

FOREIGN PATENT DOCUMENTS

| EP | 0 798 561 | 10/1997 |
| EP | 1120646 A1 | 2/2001 |
| JP | 10-146183 | 6/1998 |
| WO | WO 93/22678 | 11/1993 |
| WO | WO 99/27355 | 6/1999 |
| WO | WO 99/51778 | 10/1999 |
| WO | WO 99/67628 | 12/1999 |

OTHER PUBLICATIONS

J. Wang, et al., Biosensors & Bioelectronics, vol. 12, No. 7, pp. 587-599, XP-002113741, "Nucleic-Acid Immobilization, Recognition and Detection at Chronopotentiometric DNA Chips", 1997.
JPO Computer Translation of JP 10146183 A (Hashimoto, et al.).
U.S. Appl. No. 11/514,894, filed Sep. 5, 2006, Takahashi et al.

* cited by examiner

*Primary Examiner*—Alex Noguerola
(74) *Attorney, Agent, or Firm*—Oblon, Spivak, McClelland, Maier & Neustadt, P.C.

(57) ABSTRACT

A nucleic acid detection sensor comprises a plurality of nucleic acid chain fixed electrodes to which a probe nucleic acid chain is fixed, and a counter electrode which is arranged opposite to the nucleic acid chain fixed electrode, and a current flowing between the counter electrode and the nucleic acid chain fixed electrode.

47 Claims, 13 Drawing Sheets

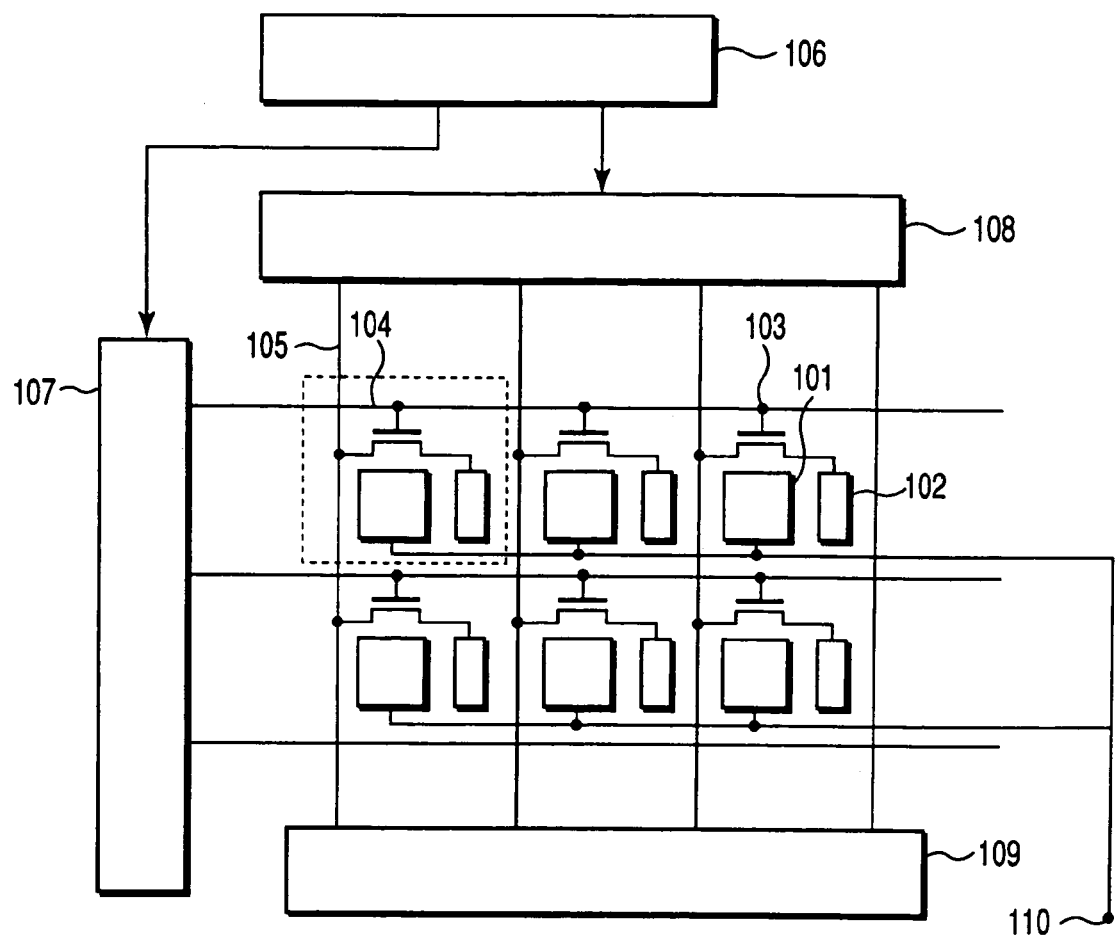
F I G. 1
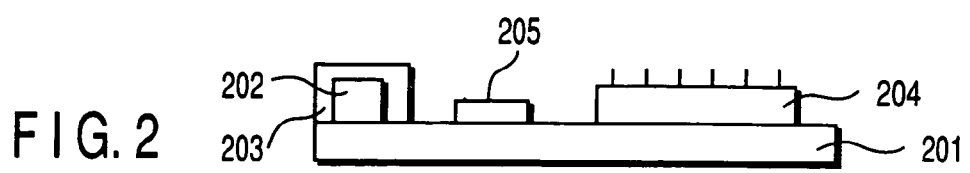
F I G. 2
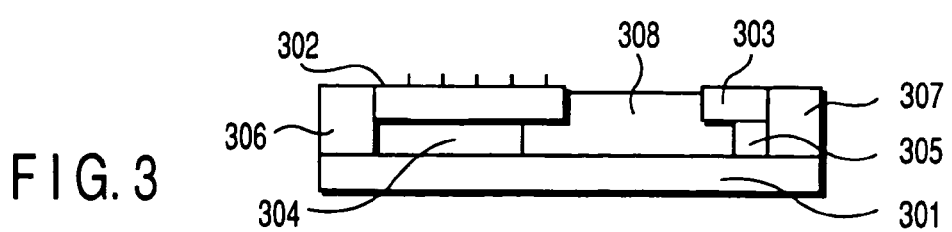
F I G. 3

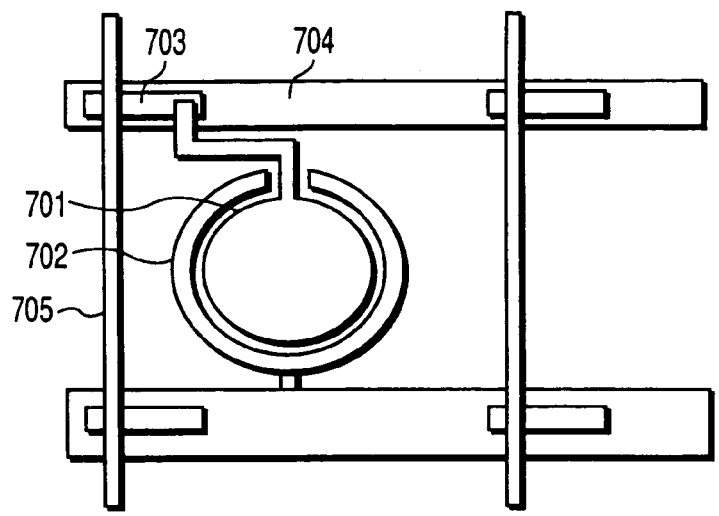
FIG. 7
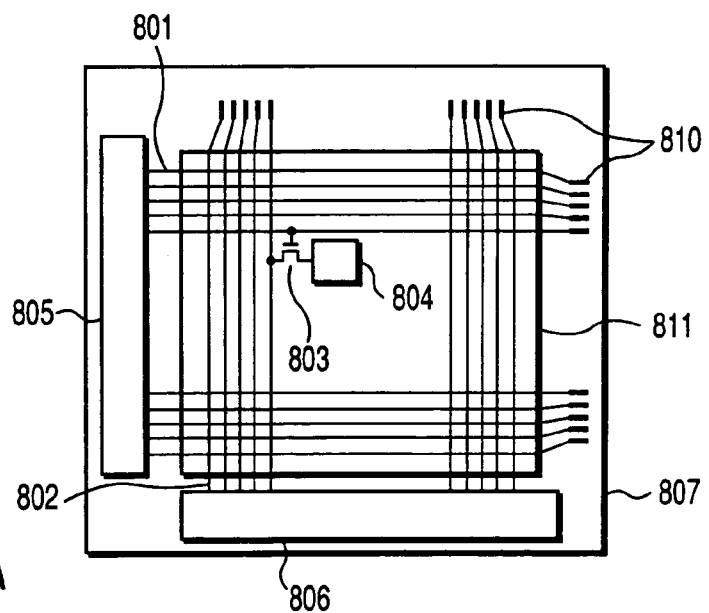
FIG. 8A
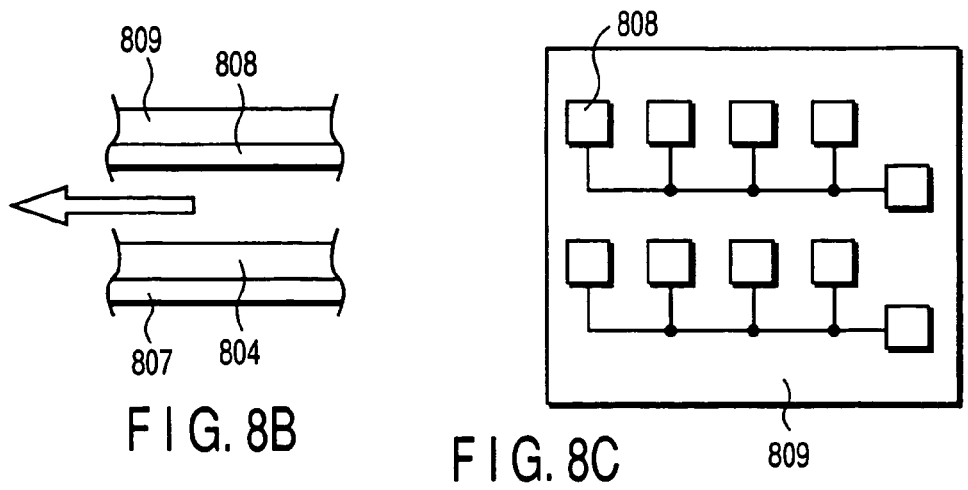
FIG. 8B
FIG. 8C

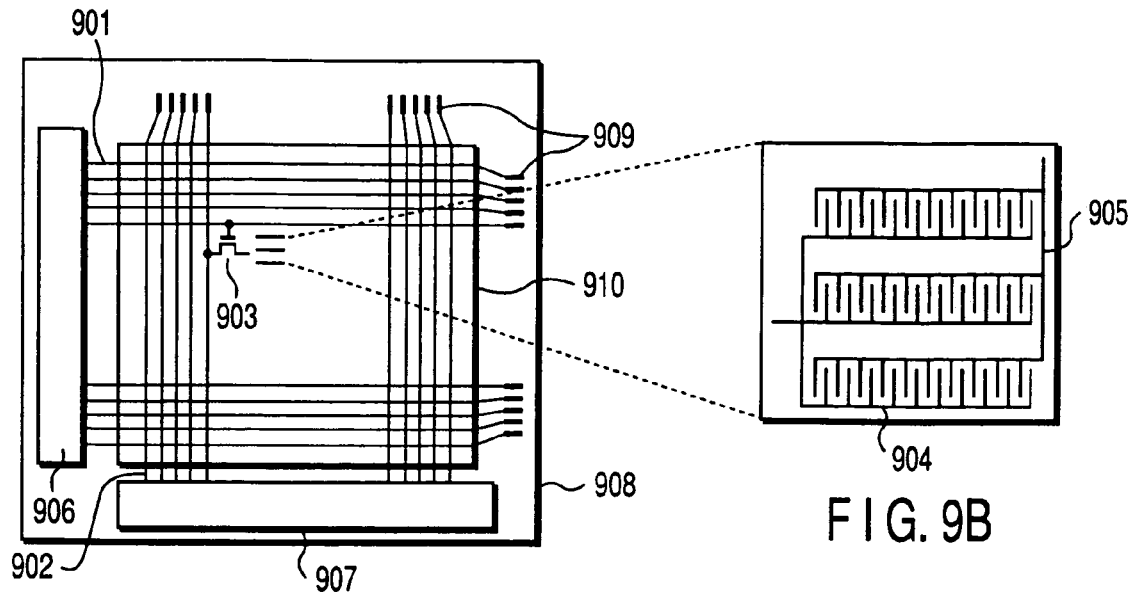
FIG. 9A
FIG. 9B
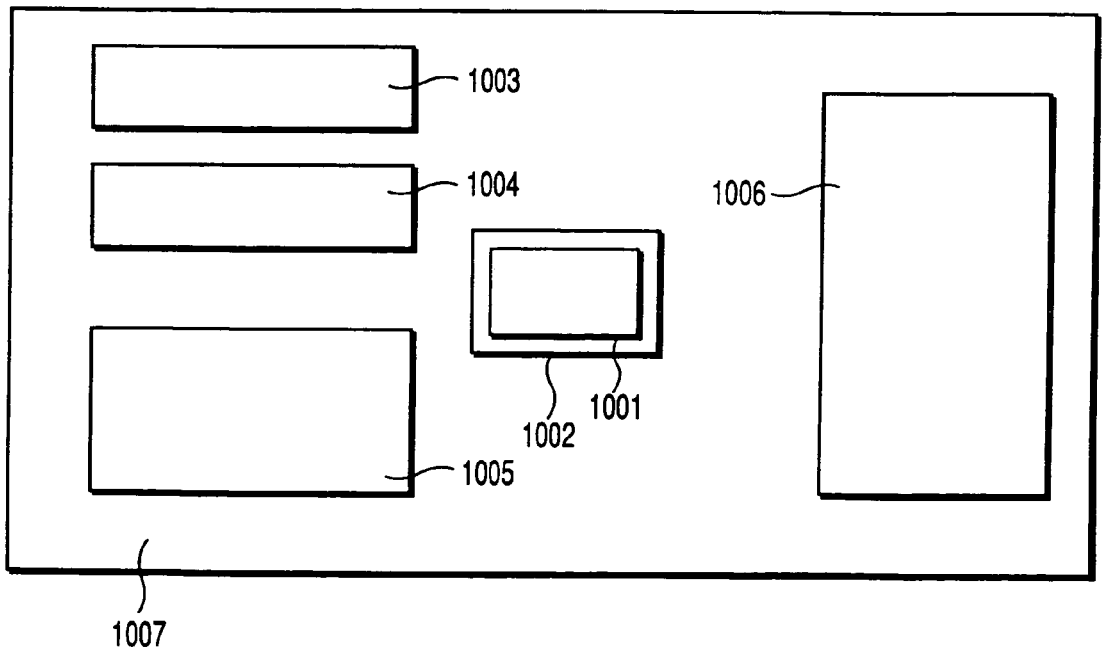
FIG. 10

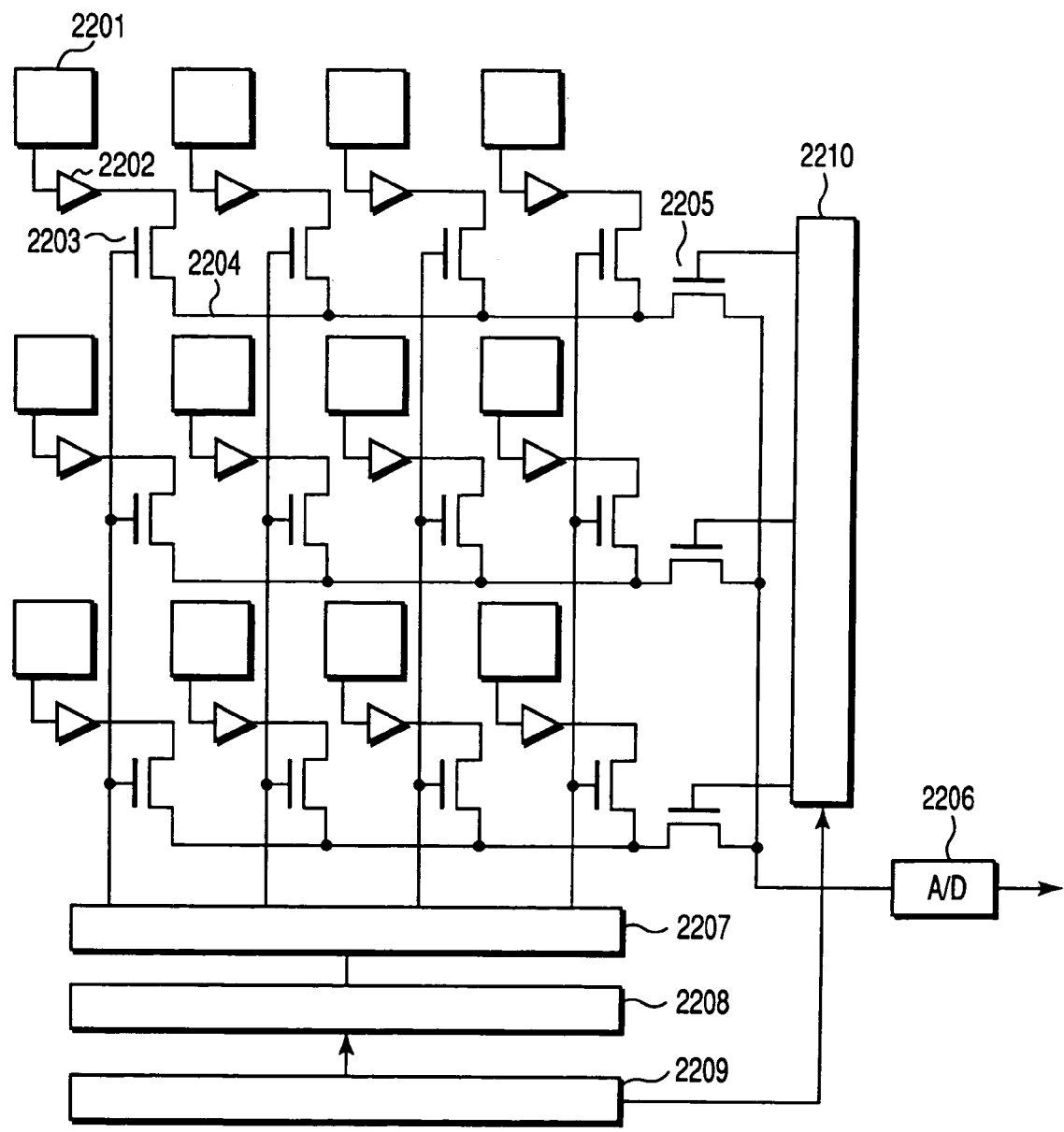
F I G. 21

NUCLEIC ACID DETECTION SENSOR

CROSS-REFERENCE TO RELATED APPLICATION

This application is a divisional application of U.S. application Ser. No. 09/961,249 filed Sep. 25, 2001 now U.S. Pat. No. 6,818,109, and based upon and claims the benefit of priority under 35 U.S.C. § 119 to Japanese Patent Application No. 2000-301516, filed Sep. 29, 2000, the entire contents each of which are incorporated herein by reference.

BACKGROUND OF THE INVENTION

1. Field of the Invention

The present invention relates to a nucleic acid detection sensor which electrochemically detects whether a target nucleic acid chain in a test liquid has a specific base sequence.

2. Description of the Related Art

Recently, a genetic test technique with a nucleic acid chain fixed array (DNA array) is made attention as a nucleic acid detection sensor (see "Beattie et al. 1993, Fodor et al. 1991, Khrapko et al. 1989, Southern et al. 1994").

DNA array indicates the array of a glass and a silicon with several cm squares where DNAs with different $10^1$ to $10^5$ kinds of arrays is fixed. The signed test liquid gene is reacted with a fluorescent dye and a radioisotope (RI), etc. on the array, or the unsigned test liquid gene and the compound of the sign oligonucleotide are reacted by the sandwich hybridization. When a complementary array to the DNA on the array exists in the test liquid, the signal (fluorescent intensity and RI intensity) which is derived from the sign by a specific part on the array is obtained. If the arrangement and the position of the fixed DNA are known beforehand, the base sequence which exists in the test liquid gene can be easily checked. Since a lot of information on the base sequence with the small amount sample can be obtained, DNA array is expected very much not only in the gene detection technique and also in the sequence technical (see "Pease et al. 1994, Parinov et al. 1996").

There are a fluorescent detection method, RI intensity detection method, and an electrochemical detection method, etc. as a technique which detects the nucleic acid which is combined with the nucleic acid detection sensor. A sign of the sample gene and a complex system are not required in an electrochemical technique. Therefore, the miniaturization of the system can be expected. In addition, since the electrode used, the electrochemical technique has an advantage that an electric reactive control can be easily performed.

Especially, among the nucleic acid detection sensors which use an electrochemical technique, the sensor having a DNA array configuration in which a plurality of electrodes where a different probe nucleic acid chain is fixed are arranged in a X-Y matrix is expected as an extremely useful technical which can detect many kinds of nucleic acids with a short time. However, the equal voltage should be applied to a lot of nucleic acid chain fixed electrodes in this sensor. Therefore, this sensor has the problems such as the circuit configuration is complex, and the response speed and accuracy are not sufficient.

BRIEF SUMMARY OF THE INVENTION

An object of the present invention is to provide a nucleic acid detection sensor which can detect many kinds of nucleic acids with high-speed and high-accuracy.

A first nucleic acid detection sensor according to the present invention is characterized by comprising: a plurality of nucleic acid chain fixed electrodes to which a probe nucleic acid chain is fixed; and a counter electrode which is arranged opposite to the nucleic acid chain fixed electrode, wherein a current flowing between the counter electrode and the nucleic acid chain fixed electrode. Since the nucleic acid chain fixed electrode and the counter electrode are opposing arranged, the measurement of high accuracy can be promptly performed by the decreased amount of the test liquid.

A second nucleic acid detection sensor according to the present invention by comprising: a plurality of nucleic acid chain fixed electrodes to which the probe nucleic acid chain is fixed; a counter electrode, a current flowing between each of the nucleic acid chain fixed electrodes and the counter electrode; and a reference electrode provided for each of the nucleic acid chain fixed electrodes, configured to make a voltage between the nucleic acid chain fixed electrode and the counter electrode constant. The measurement sensitivity is improved since the reference electrode is arranged for each nucleic acid chain fixed electrode.

A the third nucleic acid detection sensor according to the present invention by comprising: a plurality of nucleic acid chain fixed electrode, to which a probe nucleic acid chain is fixed, arranged in a matrix; a plurality of scanning lines configured to select the plurality of nucleic acid chain fixed electrodes one by one; a plurality of signal lines configured to transmit a measurement signal from the plurality of nucleic acid chain fixed electrodes; a plurality of switching elements connected with the plurality of signal lines; and aft A/D converter connected with the plurality of switching elements. The configuration becomes simple since only one A/D converter is prepared because the output line of the signal is shared with the switching element.

BRIEF DESCRIPTION OF THE SEVERAL VIEWS OF THE DRAWING

FIG. 1 is a schematic diagram which shows a nucleic acid detection chip according to the embodiment of the present invention in which a plurality of electrodes are arranged;

FIG. 2 is a figure, which shows an arrangement of an electrode in a nucleic acid detection chip according to the embodiment of the present invention and the signal line;

FIG. 3 is a figure, which shows an another arrangement of an electrode in a nucleic acid detection chip according to the embodiment of the present invention and the signal line;

FIG. 7 is an expansion figure of a unit division of a nucleic acid detection chip according to the embodiment of the present invention where the plurality of electrode is arranged;

FIG. 8A to FIG. 8C are figures which show the nucleic acid detection chip which can be installed in the nucleic acid detection system;

FIG. 9A and FIG. 9B are figures which show a nucleic acid detection chip which can be attached to the nucleic acid detection system;

FIG. 10 is a figure, which shows a nucleic acid detection system to which the nucleic acid detection chips are arranged;

FIG. 21 is a figure, which shows a wiring in a nucleic acid detection chip according to the embodiment of the present invention in which electrodes are arranged at the opposite positions.

DETAILED DESCRIPTION OF THE INVENTION

Figure 4:
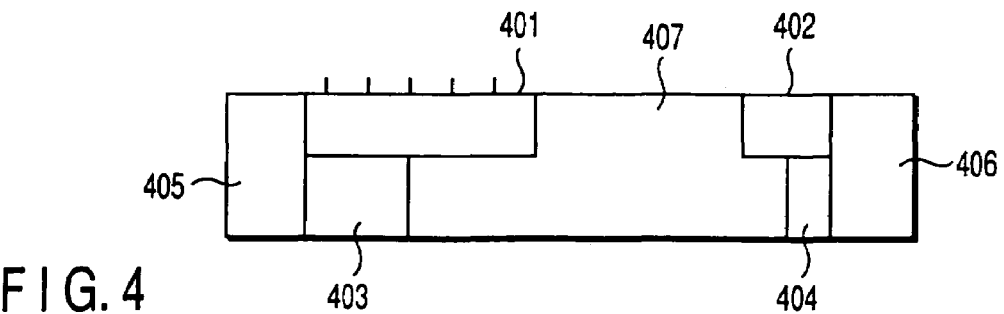
FIG. 4 is a figure, which shows an another arrangement of an electrode in a nucleic acid detection chip according to the embodiment of the present invention and the signal line.

The nucleic acid detection sensor according to embodiment of present invention is characterized by comprising each of the following configurations.

(1) The nucleic acid chain fixed electrode and the counter electrode are oppositely arranged.

(2) The reference electrodes are arranged for each cell.

(3) The output line of the signal is shared with the switching element.

In the specification, in the nucleic acid detection sensor according to the present invention to which a plurality of nucleic acid chain fixed electrodes is arranged, a "nucleic acid detection cell" means the unit division (unit cell) which comprises a couple of a nucleic acid chain fixed electrode and a counter electrode.

The probe nucleic acid chain is fixed to hybridize the target nucleic acid chain in the test liquid to the nucleic acid chain fixed electrode. The nucleic acid chain fixed electrode functions as an action electrode in the nucleic acid detection sensor according to the present invention. A "probe nucleic acid chain" indicates the nucleic acid chain fixed (combined) to the nucleic acid chain fixed electrode. A "target nucleic acid chain" is a nucleic acid chain which has a complementary base sequence for said probe nucleic acid chain and reacts the hybridization with said probe nucleic acid chain, and means the nucleic acid chain included in the test liquid.

The counter electrode functions as an auxiliary electrode to flow the current which flows between nucleic acid chain fixed electrodes. In addition, the measurement method of the nucleic acid detection cell of the nucleic acid detection sensor according to the present invention may be duplex system which uses the nucleic acid chain fixed electrode and the counter electrode, applies an arbitrary voltage between the nucleic acid chain fixed electrode and the counter electrode, and detects an electrochemical change generated between both electrodes. The measurement thereof may be an electrochemical measurement using triode system to connect a reference electrode with the nucleic acid chain fixed electrode and the counter electrode of the duplex system. Since the current flows to the counter electrode in the duplex system, there is a disadvantage that the concentration of the carrier in the electrode/interface, which determines the potential of the counter electrode, changes and the potential, which becomes a reference, changes. On the other hand, in triode system, the potential (potential of the reference electrode) which becomes a reference does not change, since the current flows between the nucleic acid chain fixed electrode and the counter electrode, the current hardly flows between the nucleic acid chain fixed electrode and the reference electrode and between the counter electrode and the reference electrode, and the voltage is applied between the nucleic acid chain fixed electrode and the counter electrode so that the desired potential may be applied to the reference electrode.

The finding of the target nucleic acid chain or the probe nucleic acid chain is obtained with the nucleic acid detection sensor according to the present invention as follows. The voltage is applied between the nucleic acid chain fixed electrode and the counter electrode in the nucleic acid detection cell in the existence of the test liquid including the nucleic acid chain. After the hybridization is occurred between the target nucleic acid chain and the probe nucleic acid chain, an electrochemical change generated between electrodes is detected. An electrochemical change is generated between electrodes if the target nucleic acid chain is hybridized with the probe nucleic acid. Therefore, if the corresponding change is detected whether the probe nucleic acid chain or the target nucleic acid chain has a specific base sequence can be detected. It is preferable that an electrochemical change generated between electrodes because of the above-mentioned hybridization is a current change which adds two chain recognition bodies in the test liquid, and derives from the two chemical change of the chain recognition body. As a result, the measurement can be performed with ease and high accuracy.

The nucleic acid chain having a known base sequence is used as a probe nucleic acid chain to be fixed to the nucleic acid chain fixed electrode. Whether the target nucleic acid chain, which reacts the hybridization in the test liquid with said probe nucleic acid chain exists may be detected. The nucleic acid chain with an unknown base sequence as a probe nucleic acid chain to be fixed to the nucleic acid chain fixed electrode is used. Whether or not the target nucleic acid chain which reacts the hybridization in test liquid with said probe nucleic acid chain exists is detected by containing the nucleic acid chain having a—known base sequence in test liquid. Thus, the finding of the array of the probe nucleic acid chain with the unknown base sequence can be obtained.

Typically, a different kind of the probe nucleic acid chain is fixed to each of the plurality of nucleic acid chain fixed electrodes. To supply different samples in each cell and perform the check of several samples at a time, the same kind of probe nucleic acid chain may be fixed.

Since one nucleic acid chain fixed electrode is arranged to the each nucleic acid detection cell, the finding of the array of the target nucleic acid chain or the probe nucleic acid chain is obtained. By checking the target nucleic acid chain hybridize to the nucleic acid detection cell. Therefore, it is preferable to arrange a switching circuit, a decoder circuit, or, a timing circuit to apply the electric signal to each nucleic acid chain fixed electrode of each cell, a circuit which outputs an electric signal from each nucleic acid chain fixed electrode, and a switching circuit to output an electric signal from each nucleic acid chain fixed electrode to an external device to operate the each nucleic acid detection cell independently.

The plurality of scanning lines are connected with the circuit such as the switching circuits to apply an electric signal to each nucleic acid chain fixed electrode of each cell. The signal to turn on the transistor, desirably, a switching element such as a thin film transistor, arranged between the nucleic acid chain fixed electrode and the signal line is applied to the scanning line. A "signal line" means a conductor line which transfers the signal specifying an electric change from the nucleic acid chain fixed electrode. The nucleic acid chain fixed electrode is an action electrode in this specification. The voltage is applied to the nucleic acid chain fixed electrode when the switching element is turned on according to the signal from the scanning line, then an electrochemical change is occurred. The change in the voltage (and/or current) by the electrochemical change is transmitted by the signal line. It is preferable to use the matrix system used to display the liquid crystal in the control of the plurality of electrodes, particular. Furthermore, it is preferable that there is an active matrix system to use the MOSFET. The scanning circuit of the MOS image sensor type can be used.

FIG. 1 shows the structure of the typical nucleic acid detection sensor which comprises the circuit to apply the voltage to each nucleic acid chain fixed electrode. FIG. 1 shows a case of measurement system of a two-electrode system. The switching element 103 connected with each nucleic acid chain fixed electrode 102 turns off and on by the signal being output to the scanning line driving circuit 107 in order to drive the scanning line 104 from the timing circuit 106 one by one in the nucleic acid detection sensor of FIG. 1. The counter electrode is connected with the power supply (not shown in the figure) through the pontiostat circuit 110. The voltage is applied to the nucleic acid chain fixed electrode 102 and counter electrode 101 when the switching element 103 opens and closes one by one. As a result, the nucleic acid (not shown in the figure) which hybridizes to the nucleic acid chain fixed electrode 102 can be detected electrochemically. An electrochemical change is transferred to the signal detection circuit 109 through the signal line 105 and is detected.

The signal line is preferably coated with the insulation material excluding the contact with the switching element as shown in FIG. 2. FIG. 2 is side figure when the cell (rectangle with dotted line) for the nucleic acid detection in the nucleic acid detection sensor of FIG. 1 is cut along parallel to the scanning line to cross the nucleic acid chain fixed electrode and the counter electrode. In FIG. 2, the signal line 202 coated by the insulation film 203, the nucleic acid chain fixed electrode 204, and the counter electrode 205 are arranged on the insulation substrate 201. Since the signal line 202 is soaked in the test liquid, the signal line 202 is coated by the insulation film 203 excluding the contact of the signal line 202 and the switching element (not shown in the figure: contact).

The arrangement of the signal line coated with the insulation material, the switching element, and the electrode is not limited to the arrangement of FIG. 2, but may be arbitrary arrangement. FIG. 3 is an example of such an arrangement, and switching elements 304 and 305 are respectively put under the nucleic acid chain fixed electrode 302 and the counter electrode 303 (or, reference electrode) arranged on the insulation substrate 301. The switching elements 304 and 305 are coated by the insulation films 306 and 307 which exist respectively on both sides thereof. Since the contact part of the signal line (not shown in the figure) and the switching element is not contacted with the test liquid 308 even when the test liquid 308 is added on the nucleic acid chain fixed electrode and the counter electrode if the switching element is put under each electrode as shown in FIG. 3, it is excellent in insulation properties. The arrangement of FIG. 4 also has the excellent insulation properties, since the switching element is put under each electrode as well as FIG. 3. But, the point in which the switching element is exposed to the rear surface of the substrate differs from the arrangement of FIG. 3.

It is preferable that each electrode which constructs the nucleic acid detection cell is formed on the insulation substrate. As a material of the insulation substrate, for example, inorganic insulation materials such as glass, fused silica, silicon, alumina, sapphire, forsterite, and silicon carbide, silicon oxide, and silicon nitride, or, organic materials such as polyethylene, ethylene, polypropylene, polyisobutylene, polyethylene terephthalate, no saturation polyester, include fluorine resin, polyvinyl chloride, polyvinylidene chloride, polyvinyl acetate, polyvinyl alcohol, polyvinyl acetal, acrylic resin, polyacrylonitrile, polystyrene, acetal, polycarbonate, polyamide, phenol resin, urea resin, epoxy resin, and melamine resin, styrene acrylonitrile copolymer, acrylonitrile butadiene styrene copolymer, silicon resin, polyphenylene oxide, and polysulfone can be used, but the material is not limited to these materials.

It is preferable that each electrode and the circuit, etc. are separated by the insulation material. The insulation material used by the present invention is not limited, but it is preferable to use photo polymer, and a photoresist material. The photoresist for an optical exposure, the photoresist for the far ultraviolet, and the photoresist for X-ray and the photoresist for the electron beam are used as a resist material. The photoresist for an optical exposure includes cyclized rubber, the polycinnamic acid, and the novolac resin as a main raw material. Cyclized rubber, phenol resin, polymethyl isopropenyl ketone (PMIPK), and polymethyl methacrylate (PMMA), etc. are used for the photoresist for the far ultraviolet. The material of the description in the "Thin Film Handbook" (Ohmsha, Ltd.) in addition to COP and the metal acrylate can be used for resist for X-ray. In addition, the material of the description can be used for the above-mentioned document such as PMMA in resist for the electron beam. It is preferable that the resist used here is 1 mm or less and more than 100 Å. It becomes possible to make the area constant by covering the electrode with the photoresist, and performing the lithography. As a result, the fixed amount of the probe nucleic acid chain becomes uniform between each electrode, and an excellent measurement in reproducibility is enabled. Conventionally, it is general to remove the resist material finally, but the resist material may be used as a part of the electrode without removing in the nucleic acid chain fixed electrode. In this case, it is necessary to use a high water-proof material for the resist material to be used. A material excluding the photoresist material may be used as the insulation layer formed on the upper portion of the electrode. For example, oxide, nitride, carbide, and other alloy of Si, Ti, Al, Zn, Pb, Cd, W, and Mo, Cr, Ta, and Ni, etc. may be used. After forming a thin film by using a sputter, an evaporation or a CVD etc. from these materials, the electrode exposure part is patterned by the photo lithography and the area is constantly controlled.

Preferably, $10^1$ to $10^5$ nucleic acid chain fixed electrodes are arranged on the insulation substrate. The material of a desirable nucleic acid chain fixed electrode is gold, and other materials can be used, for example, metal single substance such as alloy of gold, silver, platinum, mercury, nickel, palladium, silicon, germanium, gallium, and tungsten and alloy thereof, or, carbon etc. such as graphite and glassycarbon, or, oxide and compound thereof may be used. These electrodes can be manufactured by a plating, a print, a sputter, and an evaporation, etc. When the evaporation is performed, the electrode film can be formed with the resistive heating method, the high frequency heating method, and the electron beam heating method. The electrode film can be formed by a DC two poles sputtering, a bias sputtering, an asymmetric AC sputtering, a gettering sputtering, and a high frequency sputtering when the sputtering is used. Here, when the gold is used for the electrode, the orientation index in a (111) plane of the crystal structure of the gold is important. The orientation index is obtained from the following equations by the method of Willson.

Orientation index $(hkl) = IF_{(hkl)}/IFR_{(hkl)}$

Hkl; plane index $IF_{(hkl)}$; Relative intensity in (hkl) plane $IFR_{(hkl)}$; $IF_{(hkl)}$ as standard gold described in ASTM card Here, in case of the nucleic acid chain fixed electrode for the nucleic acid chain detection, it is required that the orientation index is one or more, in addition, it is preferable that the orientation index is two or more. It is also valid to heat the substrate to improve the orientation at the evaporation or the sputtering. It is preferable that the heating temperature is a range of 50° C. to 500° C., though the heating temperature is not limited. It becomes possible to uniformly control the nucleic acid chain fixed amount by controlling the orientation. When the above-mentioned electrode material of the gold etc. are evaporated or sputtered to the substrate such as the glass, it becomes possible to form a stable electrode layer by existing titanium or chrome, copper, nickel, and alloy thereof solely or by combining between the substrate and the gold as a bonding layer.

Figure 5:
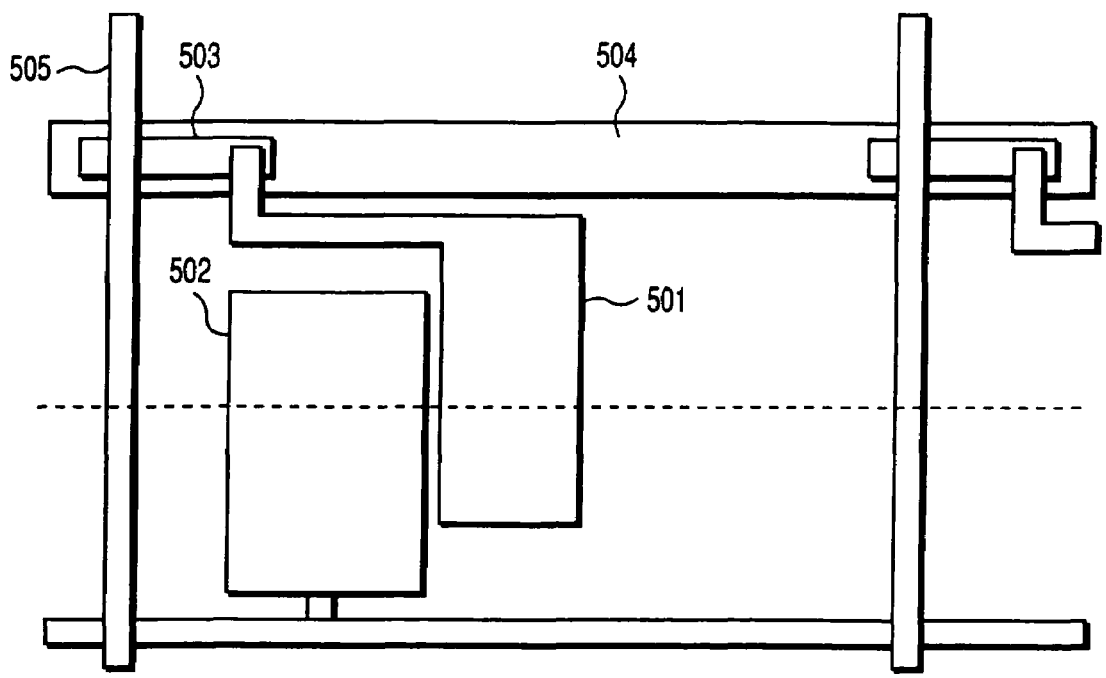
FIG. 5 is an expansion figure of a unit division of a nucleic acid detection chip according to the embodiment of the present invention where the plurality of electrode is arranged.
Figure 6:
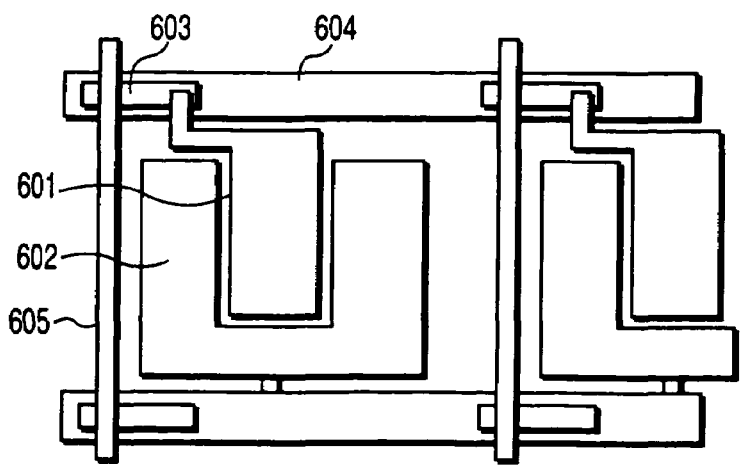
FIG. 6 is an expansion figure of a unit division of a nucleic acid detection chip according to the embodiment of the present invention where the plurality of electrode is arranged.

The shape of the nucleic acid chain fixed electrode is not the limited, and the shapes shown in FIG. 5 to FIG. 7 are preferable. It is advantageous since the contact area of the nucleic acid fixed electrode and the counter electrode (or, reference electrode) is large if the shapes of FIG. 6 and FIG. 7 are used. FIG. 5 to FIG. 7 are figures which expand the nucleic acid detection cell (rectangle of dotted line in FIG. 1). As well as FIG. 1, the nucleic acid chain fixed electrodes 501, 601 and 701 are connected with the signal lines 505, 605 and 705 through the switching elements 503, 603 and 703, respectively. The counter electrodes (or, reference electrode) 502, 602 and 702 is arranged in the neighborhood of the nucleic acid chain fixed electrodes 501, 601 and 701.

It is preferable to activate the surface of the electrode to fix the probe nucleic acid chain to the nucleic acid chain fixed electrode. Activation can be performed by the potential sweep in the sulfuric acid solution. Activation can be performed even by the mixed acid and the aqua regia, etc. The material which constructs the probe nucleic acid chain is not limited, but DNA, RNA, PNA, and other nucleic acids analog can be used.

The method of fixing the probe nucleic acid chain is not especially limited. For example, it is possible to perform fixation easily by using the bond of the thiol radical and gold which are introduced into the probe nucleic acid chain. Additionally, it is possible to perform fixation by physical adsorption, chemical adsorption, the canal bond, embedding, and the covalent bond, etc. The condensation medicines such as the biotin-avidin bonds and carbodiimides can be used. Fixation can be facilitated by modifying the surface of the electrode with the molecule having the functional group beforehand in these cases. In addition, to control non-peculiar adsorption of a nucleic acid to the surface of the electrode and the intorcalators etc., it is preferable to cover the surface of the electrode with the mercaptan such as mercaptoethanols and lipids such as stearylamides.

Hereinafter, the method of fixing the probe nucleic acid chain to the nucleic acid chain fixed electrode which consists of gold will be described as an example. After washing by the demineralized water, the electrode performs the activation processing. The sulfuric acid solution of 0.1 to 10 mmol/L is used for activation. Potential is scanned in this solution within the range of 1 v/s to 100,000 v/s within the range of −0.5 to 2V (vs Ag/AgCl). As a result, the surface of the electrode is activated to the state that the probe nucleic acid chain can be fixed. The thiol radical is introduced to 5' or 3' end of the probe nucleic acid chain used for fixation. The probe nucleic acid chain made a thiol dissolves to the solution of the reducer such as DTT immediately before fixation, and removes DTT by the extraction operation with the gel filtration or the acetic acid ethyl etc. immediately before use. Fixation is very easy. The probe nucleic acid chain is dissolved in the buffer liquid within the range of pH5 to pH10 as becoming within the range of 1 ng/mL to 1 mg/mL within the range of ion intensity of 0.01 to 5. The activated electrode is soaked. The reaction of fixation is performed for about ten minutes to around one evening within the range of 4 to 100° C.

It is preferable to store the electrode after fixing the probe nucleic acid chain in the condition where the nucleic acid decomposition ferment (nuclease) does not exist, and by shading if possible. However, when it is short-term, it is possible to be stored in the wet condition. It is preferable that the composition of the medium is a composition of the liquid to which the hybridization reacts, Tris-EDTA buffer liquid, or demineralized water. It is preferable that the storage temperature is 4° C. or less, preferably, −20° C. When the nucleic acid chain fixed electrode to which the probe nucleic acid chain is fixed is stored at a long term, it is preferable to store in a dry condition. It is possible to perform dry with freeze-drying and air drying, etc., though the method of keeping to dry is not especially limited. It is preferable that it is an inert gas, nitrogen, dry air such as argon or a vacuum, though gas phase of dry is not especially limited.

The operativeness of the test can be raised by putting the sign or the bar code on each electrode.

The probe nucleic acid chain can be fixed comparatively easily with a device of fixation which is called DNA spotter and DNA arrayer at the time of fixing the probe nucleic acid chain on the electrode. In this case, it is preferable to use the spotter of an ink jet system or an electrostatic system to prevent the surface of the electrode from being damaged. It is also possible to synthesize the nucleic acid chain directly on the surface of the electrode.

One or more counter electrodes are arranged on the nucleic acid detection sensor according to the present invention. When a single counter electrode is arranged, the plurality of nucleic acid chain fixed electrodes commonly use a single counter electrode.

If the desired voltage can be applied to the nucleic acid chain fixed electrode, the distance of the nucleic acid chain fixed electrode and the counter electrode is not especially limited. It is preferable to arrange the distance within 1 cm, for example, to make the response speed fast.

It is desirable to arrange the counter electrode to become an equal distance from all the nucleic acid chain fixed electrodes in order to apply an equal voltage to all the nucleic acid chain fixed electrodes.

The material is not especially limited to the material used for the counter electrode, and the material used by the nucleic acid chain fixed electrode can be used.

When the nucleic acid detection sensor according to the present invention is measured by the triode system, the reference electrode is arranged. The silver/silver chloride electrode, mercury/mercury chloride electrodes, etc. can be used as a reference electrode, but other arbitrary electrodes can be used.

It is general to arrange the counter electrode or the reference electrode in the same substrate as the nucleic acid chain fixed electrode, but the counter electrode or the reference electrode may be arranged in the part excluding this.

Since the measurement accuracy is improved, it is desirable that a shape of reference electrode is a shape of enlarging the surface area and preventing the flow of test liquid from obstructing, though the shape thereof is not especially limited. For example, electrodes suit such a condition by making the reference electrode and the nucleic acid chain fixed electrode a comb shape in which electrodes thereof are engaged mutually.

It is preferable that the nucleic acid detection sensor according to the present invention configures the nucleic acid detection system. The corresponding system has a basic configuration comprising one or a plurality of substrates on which the plurality of nucleic acid detection cells are formed, the container which is an airtight container to hold the substrate and has at least one or more openings to transfer the liquid and a space for storing the liquid, and a terminal to connect with an external equipment.

On the system, it is preferable to comprise a circuit to apply an electric signal to the counter electrode and the nucleic acid chain fixed electrode, a switching circuit to apply an electric signal to each counter electrode and each nucleic acid chain fixed electrode, a circuit which outputs an electric signal from each nucleic acid chain fixed electrode, a switching circuit to output an electric signal from each nucleic acid chain fixed electrode outside, a power supply, a potentiostat, and a the waveform generation device. To the system, it is preferable to integrate circuits such as a decoder circuit to output an electric signal to the MOSFET switching element at specific position arranged in matrix and a nucleic acid chain fixed electrode, a switching circuit, a timing circuit, memory, an A/D converter, a waveform generation device, a power supply, a potentiostat, and an electric signal detection circuit on one sensor.

A nucleic acid extraction mechanism, a nucleic acid refinement mechanism, and a nucleic acid amplification mechanism, etc. can be integrated on the nucleic acid detection system. If the nucleic acid detection system comprising these mechanisms is used, all series of operations of the extraction, amplification, and the detection, etc. of a nucleic acid can be automatically performed.

In FIGS. 8A to 8C show an example of the nucleic acid detection sensor which can construct the nucleic acid detection system.

The nucleic acid detection sensor of FIGS. 8A to 8C comprises a plurality of scanning lines 801, signal lines 802 arranged to cross the scanning lines 801, switching elements 803 such as thin film transistors arranged to each intersection in the scanning lines 801 and the signal lines 802, nucleic acid chain fixed electrodes 804 connected with the switching elements 803, a scanning line driving circuit 805 to drive each scanning lines 801, a first substrate 807 (FIG. 8A) on which a signal line driving circuit 806 to drive each signal line 802 is arranged, and a second substrate 809 (FIG. 8C) on which each counter electrode 808 is arranged. Each counter electrode 808 is connected with the potentiostat (not shown in the figure).

Though only one nucleic acid chain fixed electrode is written in FIG. 8, actually, one nucleic acid chain fixed electrode is arranged respectively on the rectangular of each inside of the surround to two adjacent scanning line and two adjacent signal lines.

In order to detect the target nucleic acid in the test liquid, the driving signal is transmitted from the scanning line driving circuit 805 to the switching element 803, after the test liquid is injected into the space which lies between the first substrate 807 and the second substrates 809. The switching element 803 is turned on by the driving signal output from the scanning line driving circuit 805, and the nucleic acid chain fixed electrode 804 and signal line 802 are electrically connected. The voltage is applied between the nucleic acid chain fixed electrode 804 and the counter electrode 808 when the nucleic acid chain fixed electrode 804 and signal line 802 are electrically connected. As a result, for example, the stuff such as the intorcalators inserted in the target nucleic acid hybridized to the nucleic acid chain fixed electrode 804 is oxidized. The current generated by the oxidation flows to the pad 810 provided to one end of the signal line 802 through the signal line 802, and is detected and measured with an external equipment for the current detection connected with the pad 810.

In the nucleic acid detection sensor of FIG. 8, a nucleic acid detection part 811, a scanning line driving circuit 805, and a signal line driving circuit 806 are formed on the first substrate 807 integrally, and the nucleic acid detection sensor is installed to the nucleic acid detection system comprising the signal detection part and is used.

In the shape shown in FIG. 9A and FIG. 9B, the counter electrode 905 may be connected with scanning lines 901 electrically and may be arranged in the vicinity of the nucleic acid chain fixed electrode. In FIG. 9A and FIG. 9B, the counter electrode 905 has a comb shape each of whose branches are branched to three, and is arranged so as to mutually engage with the nucleic acid chain fixed electrode 905 having the same shape thereof.

Though the nucleic acid detection sensor to which the reference electrode is not provided is shown in FIG. 8A, FIG. 8B, FIG. 9A, and FIG. 9B, it is preferable to provide the reference electrode. The reference electrode may be a comb electrode which is mutually engaged to the nucleic acid chain fixed electrode, and can be god combination, float, and be type electrode in each other as shown in FIGS. 9A and 9B.

An example of the circuit of the embodiment to which the reference electrode is provided in each nucleic acid chain fixed electrode will be described later.

The outline of the nucleic acid detection system to which the nucleic acid detection sensor according to the present invention is arranged is shown in FIG. 10.

The nucleic acid detection System 1007 shown in FIG. 10 comprises a nucleic acid detection sensor 1001, a nucleic acid detection sensor fixation device 1002, an electric signal measurement device 1003, a CPU 1004, a power supply 1005, and, a display device 1006.

Figure 11A:
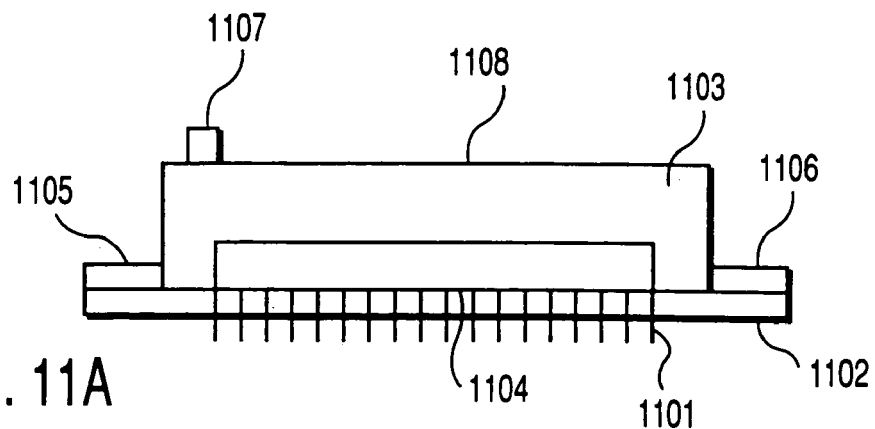
FIG. 11A and FIG. 11B are figures which show the nucleic acid detection chip according to the embodiment of the present invention stored in the container.
Figure 11B:
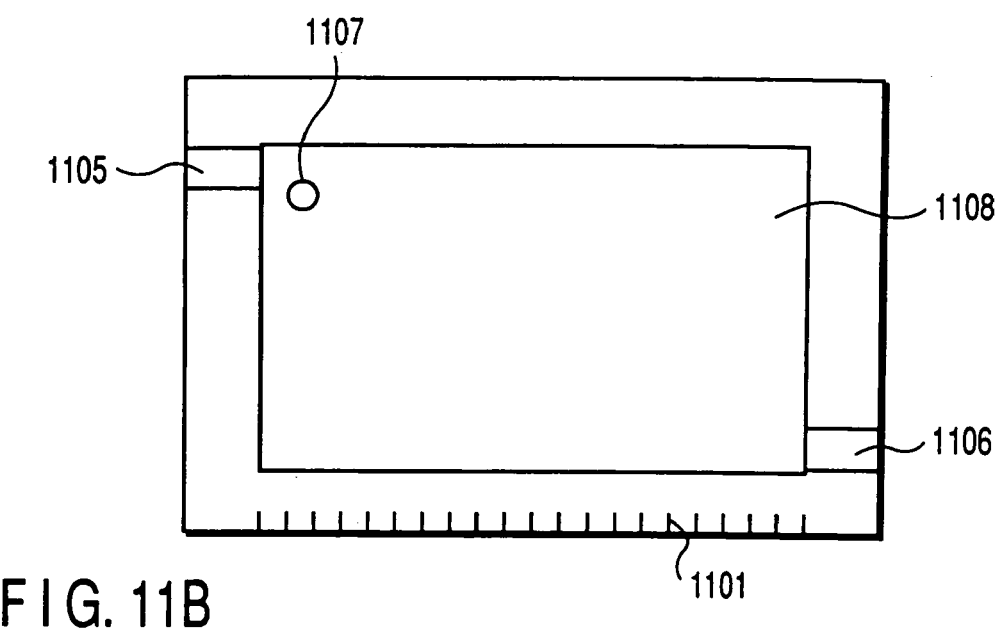
Figure 12:
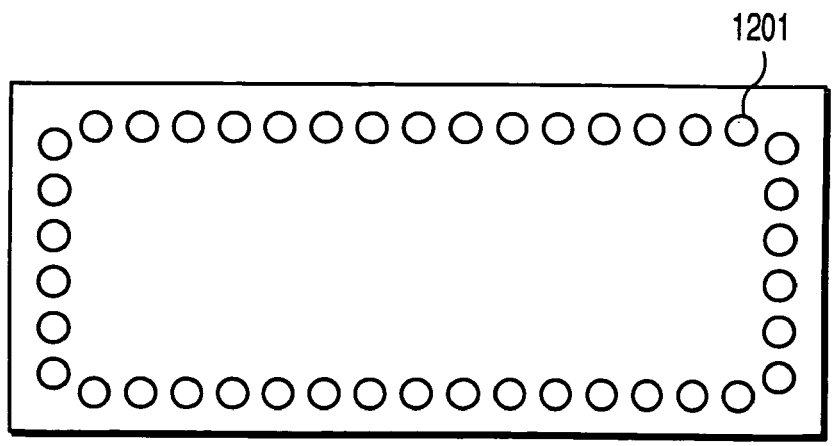
FIG. 12 is a figure, which shows the substrate to which the nucleic acid detection chip according to the embodiment of the present invention should be installed.
Figure 13A:
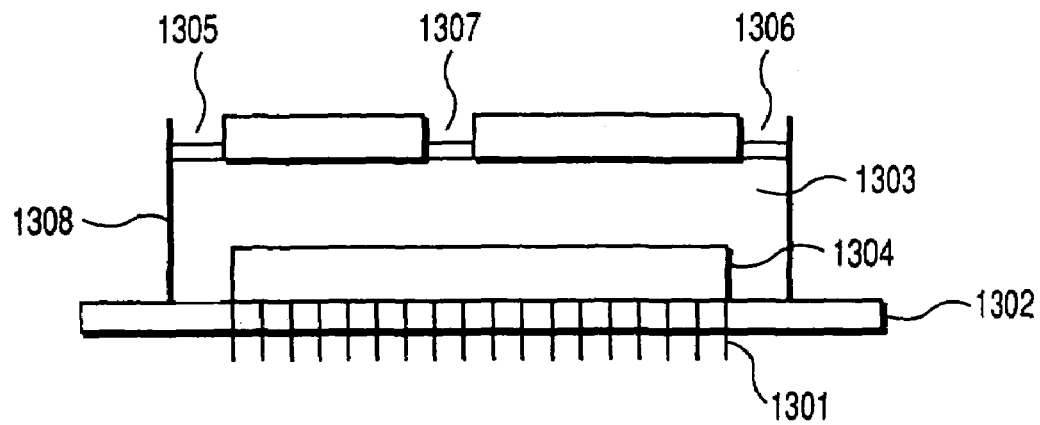
FIG. 13A and FIG. 13B are figures which show a nucleic acid detection chip according to the embodiment of the present invention stored in the container.
Figure 13B:
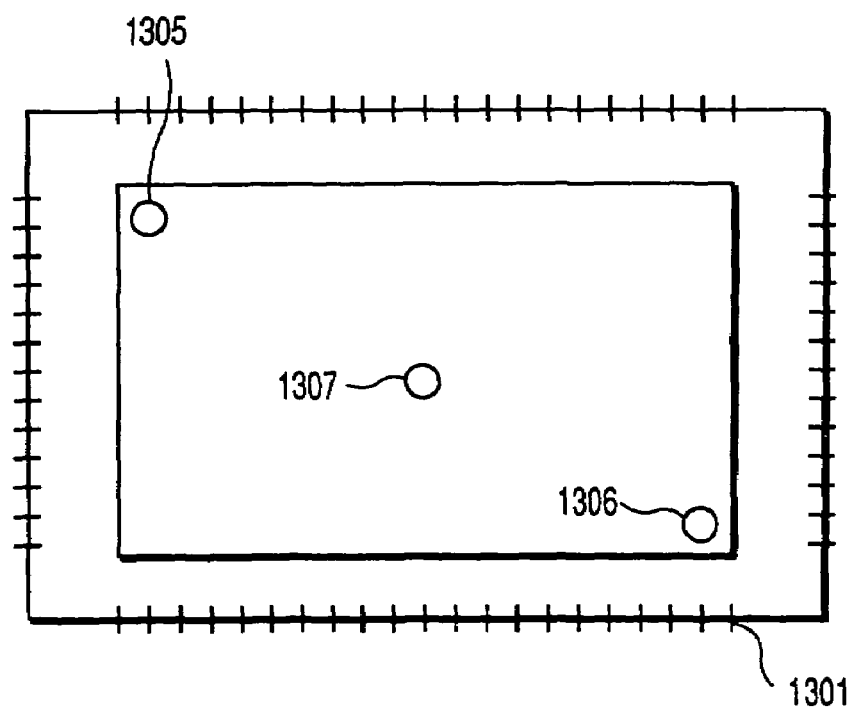

The nucleic acid detection sensor is usually attachably and detachably arranged on the substrate 1102 with the connection terminal 1101, and stored in the container 1108 as shown in FIG. 11 in the above-mentioned system. The substrate 1102 has a connection terminal insertion part 1201 in the surroundings thereof, for example, as shown in FIG. 12. In FIG. 11, the test liquid 1103 is injected from the test liquid injection entrance 1105 provided to the bottom to soak the nucleic acid detection sensor 1104 in a state of closing the test liquid outlet 1106. After the nucleic acid detection sensor 1104 is soaked with the test liquid 1103, the nucleic acid included in the test liquid 1103 is hybridized with the nucleic acid chain fixed electrode (not shown in the figure) on the nucleic acid detection sensor 1104. When the nucleic acid detection sensor 1104 is humidified while hybridizing, the evaporated test liquid is exhausted through an air hole 1107. The target nucleic acid is hybridized with the nucleic acid chain fixed electrode (not shown in the figure) on the nucleic acid detection sensor 1104 if the target nucleic acid is included in test liquid. Therefore, after the test liquid 1103 is exhausted from the test liquid outlet 1106, the test liquid 1103 keeps combining with the nucleic acid chain fixed electrode. The test liquid injection entrance 1305 and the test liquid outlet 1306 may be provided at a vertical position of substrate 1302 as shown in FIG. 13.

Hereinafter, the operation to obtain the finding of the target nucleic acid chain in the test liquid or the probe nucleic acid chain with a nucleic acid detection sensor according to the present invention will be explained in detail.

First, the test liquid including the target nucleic acid chain is injected to the space which lies between the nucleic acid chain fixed electrode and the counter electrode.

The detected target nucleic acid chain is not especially limited, and may be the nucleic acid chain of virus, bacillus, fungous, and helminth etc., a cause genes of an inherited disease, and a marker genes of various diseases etc. For example, it is possible to be used to detect virus infection syndromes such as hepatitis virus (A, B, C, D, E, F, and G type), HIV, influenza virus, herpes group virus, adenovirus, human polyoma virus, human papilloma virus, human parvovirus, mumps virus, human rotavirus, enterovirus, Japanese encephalitis virus, dengue fever virus, rubella viruses, and HTLV, bacillus infection syndromes such as yellow *staphylococcus*, hemolytic *streptococcus, escherichia coli*, enteritis vibrio, *helicobacter pylori*, campylobacter, cholera bacterium, dysentery bacterium, salmonella, senior ell, gonococcus, and squirrel terrier bacterium, leptospire, legionalla bacterium, spirochete, pneumonia mycoplasma, rickettsia, chlamydia, malaria, dysentery amoebas, and causes of a disease fungous, and helminth, fungous, parasite or fungus. It can be also used for a check of inherited disease, retina bud cell tumor, Wilm's tumor, family character large intestines polyposis, inherited non-polyposis colic cancer, neurofibroma, familial breast cancer, xeroderma pigmentosum, brain tumor, mouth cancer, gullet cancer, stomach cancer, and colic cancer, check of tumor disease such as liver cancer, pancreatic cancer, lung cancer, goiter, mastadenoma, urinary organs tumor, virilia tumor, female genital tumor, ecphyma, bone-soft part tumor, leukemia, lymphoma, solid tumor, etc. It can be adopted to all fields to which the gene check is necessary in the food check, quarantine, medicine check, legal medicine, agriculture, stock raising, fishery, and forestry, etc. besides the medical treatment. In addition, the detection of restriction fragment length polymorphism (RFLP), single nucleotide polymorphisms (SNPs), and the micro satellite array, etc. is also possible. It is also possible to use for analyzing the unknown the base sequence.

The test liquid which contains these target nucleic acids is not especially limited, for example, blood, serum, white blood corpuscle, urine, service, semen, saliva, organization, culture cell, and expectoration, etc. may be used. The nucleic acid component is usually extracted from these test liquids. The extraction method is not especially limited, and may use liquid-liquid extraction methods of phenol-chloroform method, etc. and the solid-liquid extraction methods which use carrier. It is also possible to use method QIAamp of extracting a nucleic acid on the market (made by the QIAGEN company) and Sumai-test (made by the Sumitomo Metal Industries, Ltd. company), etc.

The hybridization reaction is performed by the extracted nucleic acid component and the nucleic acid chain detection electrode after the test liquid is injected into the space. A reactive solution is performed in the buffer liquid within the range of ion intensity 0.01 to 5 and the range of pH5 to pH10. Sulfuric acid dextran, salmon sperm DNA, sweetbread DNA, EDTA, and the surface-active agent, etc. which are the hybridization promotion medicine in this solution can be added. The nucleic acid component extracted here is added, and thermal deformed at 90° C. or more. The insertion of the nucleic acid chain detection electrode can be performed immediately after deformation or after quick cooling to 0° C. A reactive speed can be improved by the operation such as the stir or shaking while reacting. A reactive temperature is within the range of 10° C. to 90° C. and a reactive time is from one minute or more to about one evening. The hybridization reaction can be controlled electrochemically and necessary time of reaction can be shortened to a few minutes by applying for the plus potential to the nucleic acid chain fixed electrode, but it is necessary from several hours to several days, conventionally. On the other hand, nonspecific bond can be removed by applying for minus potential to the surface of the electrode.

When the hybridization reaction ends, the nucleic acid chain fixed electrode is washed. The buffer liquid within the range of pH5 to pH10 and the ion intensity thereof is within the range of 0.01 to 5 is used for washing.

The duplex chain cognitive body, that is, an intercalator which selectively combines with a duplex part (hybrid of the probe nucleic acid chain and the target nucleic acid chain) formed on the surface of the electrode after washing, reacts and an electrochemical measurement is performed. The duplex chain cognitive body is a double stranded nucleic acid recognizing substance which binds specifically to a double stranded nucleic acid and is active physicochemically to the reaction system of said nucleic acid probe and said gene sample. The intercalator used here is not limited, and bisintercalator, trisintercalator, and polyintercalator, etc. such as Hoechst 33258, acridine orange, quinacrine, daunomycin, metalointercalator, and bisacridine can be used as the intorcalator. It is also possible to use the living body high molecules such as organic compounds such as metallic complex such as ruthenium which is called metalointercalator, cobalt, and iron and ethidium bromide, antibodies, and ferments.

The concentration of the intorcalator is different depending on the kind, but it is used within the range of generally 1 ng/mL to 1 mg/mL. In this case, the buffer liquid within the range of pH5 to 10 and the ion intensity within the range of 0.001 to 5 is used.

The nucleic acid chain fixed electrode is washed after reacting with the intorcalator, and an electrochemical measurement is performed. An electrochemical measurement is performed by three electrode type, that is, the reference electrode, the counter electrode and the action electrode or two electrode type, that is, the counter electrode and the action electrode. In the measurement, a potential more than a potential to which the intorcalator electrochemically reacts is applied, and the reactive current value which derives from the intorcalator is measured. In this case, the potential can be sweeped at a fixed velocity, or be applied with the pulse or can be applied with fixed potential. The current and the voltage are controlled by using devices such as potentiostat, digital multi meters, and the function generators for the measurement. The concentration of the target gene is calculated from calibration curve based on the obtained current value.

An electrochemical signal can have the oxidation reduction current change, the oxidation reduction potential change, the electric capacity change, the resist change, and the electrochemistry emission change to the index. The effect of these signal change is promoted by using the material which combines with duplex chain nucleic acid such as intorcalator etc. specifically.

The first nucleic acid detection sensor according to the present invention is characterized by arranging the nucleic acid chain fixed electrode and the counter electrode oppositely so that the test liquid may flow between the nucleic acid chain fixed electrode and the counter electrode.

Figure 14A:
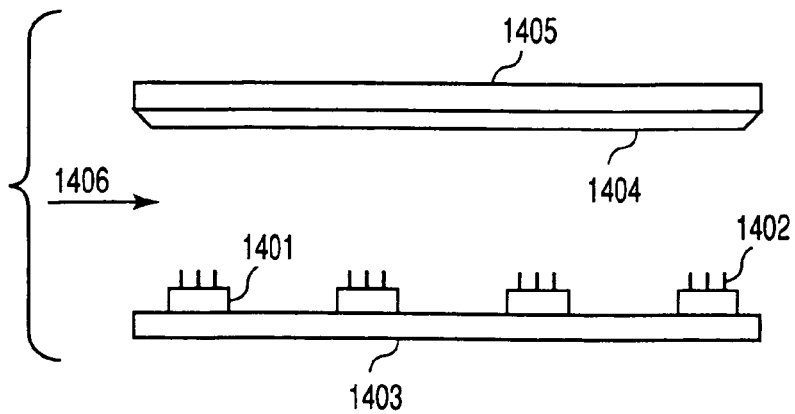
FIG. 14A to FIG. 14D are figures which compares a nucleic acid detection chip according to the embodiment of the present invention in which electrodes are arranged at opposed positions and a conventional nucleic acid detection chip in which electrodes are not arranged at opposed positions.
Figure 14B:
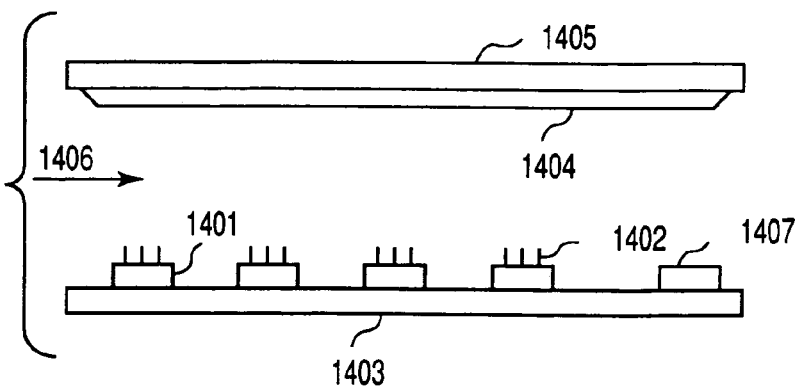
Figure 14C:
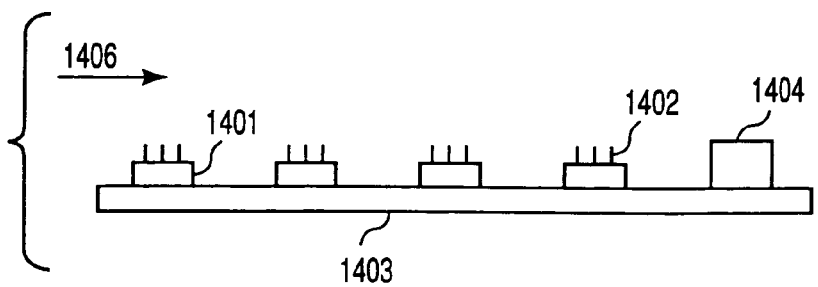
Figure 14D:
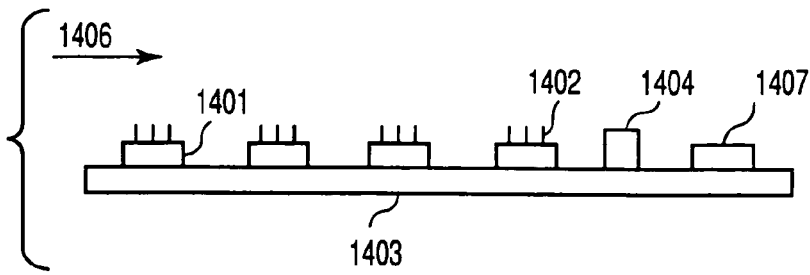

FIG. 14C and FIG. 14D show the nucleic acid detection sensors which construct the conventional DNA array. A plurality of nucleic acid chain fixed electrodes 1401, to which the probe nucleic acid chain 1402 with an already-known array is fixed, and the counter electrode 1404 are arranged on the same substrate 1403, and the test liquid 1406 flows on abovementioned substrate 1403. In the corresponding arrangement, the distance of the counter electrode 1404 and each nucleic acid chain fixed electrode 1402 is different in each nucleic acid fixed electrode 1401. In such a configuration, there is a case the distance of the nucleic acid chain fixed electrode 1401 and the counter electrode 1404 might become far as shown in the left end of the figure, and the response speed becomes slow. Since the distance of the counter electrode 1404 and each nucleic acid chain fixed electrode 1401 is different in each nucleic acid chain fixed electrode 1401, enough measurement accuracy cannot be achieved.

On the other hand, in the first nucleic acid detection sensor according to the present invention shown in FIG. 14A and FIG. 14B, the nucleic acid chain fixed electrode 1401 and the counter electrode 1404, to which the probe nucleic acid chain 1402 is fixed, are plate-like electrodes, and are arranged oppositely to grasp so that the test liquid. According to the corresponding arrangement, all of each nucleic acid chain fixed electrode 1401 on the first substrate 1403 can be arranged to an equal distance from the counter electrode 1404 on the second substrate 1405 and the neighborhood of the counter electrode 1404. Therefore, by using the nucleic acid detection sensor in which the electrodes are arranged in such a manner, it becomes possible to apply an equal voltage to all the target nucleic acids in the test liquid 1406, which is hybridized with the probe nucleic acid chain 1402 on each nucleic acid chain fixed electrode 1401, to be detected. Therefore, the measurement accuracy and the response speed improve. Since the test liquid 1306 is injected between the first substrate 1303 and the second substrates 1305, the amount of a necessary test liquid can be decreased. FIG. 14A shows the nucleic acid detection sensor that the reference electrode 1407 is not arranged on the first substrate 1403. FIG. 14B shows the nucleic acid detection sensor that the reference electrode 1407 is arranged on the first substrate 1403.

In the first nucleic acid detection sensor according to the present invention, when the nucleic acid chain fixed electrode is formed on the insulation substrate, the counter electrode is arranged to place a flow path of the test liquid with the nucleic acid chain fixed electrode, and is arranged in a substrate different from the substrate where the nucleic acid chain fixed electrode.

The position of the counter electrode and the nucleic acid chain fixed electrode is not especially limited. It is desirable to arrange the counter electrode to become an equal distance from all the nucleic acid chain fixed electrodes to apply an equal electrode to all the nucleic acid chain fixed electrodes, though both electrodes are arranged on a different substrate. For example, when the nucleic acid chain fixed electrode is arranged on a plane, the counter electrode may be arranged on a plane parallel to the plane. When the nucleic acid chain fixed electrode is arranged on the sphere, the counter electrode may be arranges on the concentric sphere of the sphere.

In the first nucleic acid detection sensor, it is preferable the both of the nucleic acid fixed electrode and the counter electrode have flat surfaces and the flat surfaces are arranged oppositely.

The first nucleic acid detection sensor according to the present invention comprises a plurality of nucleic acid detection cells, and one or more nucleic acid chain fixed electrodes is arranged in each cell. The counter electrode may be provided for each nucleic acid chain fixed electrode. The counter electrode may be common among the plurality of nucleic acid detection cells and may be one, for example, in a word, for the plurality of nucleic acid chain fixed electrodes.

The material of the counter electrode which should be arranged in the first nucleic acid detection sensor according to the present invention and the distance with the nucleic acid chain fixed electrode are the above-mentioned.

It is general to arrange the reference electrode in the same substrate as the nucleic acid fixed electrode when the reference electrode is arranged in the first nucleic acid detection sensor according to the present invention. The reference electrode may be arranged in the part excluding this.

The second nucleic acid detection sensor according to the present invention is characterized by comprising a reference electrode in each cell.

In the second nucleic acid detection sensor according to the present invention, the counter electrode may be common to the plurality of nucleic acid chain fixed electrode or may be arranged for each nucleic acid detection cell. The counter electrode may be connected with either of the signal line or scanning line when the plural connect counter electrodes are arranged.

The material of the nucleic acid chain fixed electrode, the counter electrode, and the reference electrode and the operation etc. for the measurement of nucleic acids are as being described to a general configuration of the nucleic acid detection sensor according to the present invention mentioned above and directions. That is, by using the electrochemical reaction by the hybrid nucleic acid chain formed between the probe nucleic acid chain and the target nucleic acid chain, whether or not the probe nucleic acid chain or the target nucleic acid chain has a specific base sequence is detected.

Thus, the measurement accuracy improves by decreasing the uncompensatory resistance between the nucleic acid chain fixed electrode and the reference electrode if the reference electrode is provided to each nucleic acid chain fixed electrode. It is preferable to comprise the reference electrode to each nucleic acid chain fixed electrode to control the potential of each nucleic acid chain fixed electrode.

Figure 15:
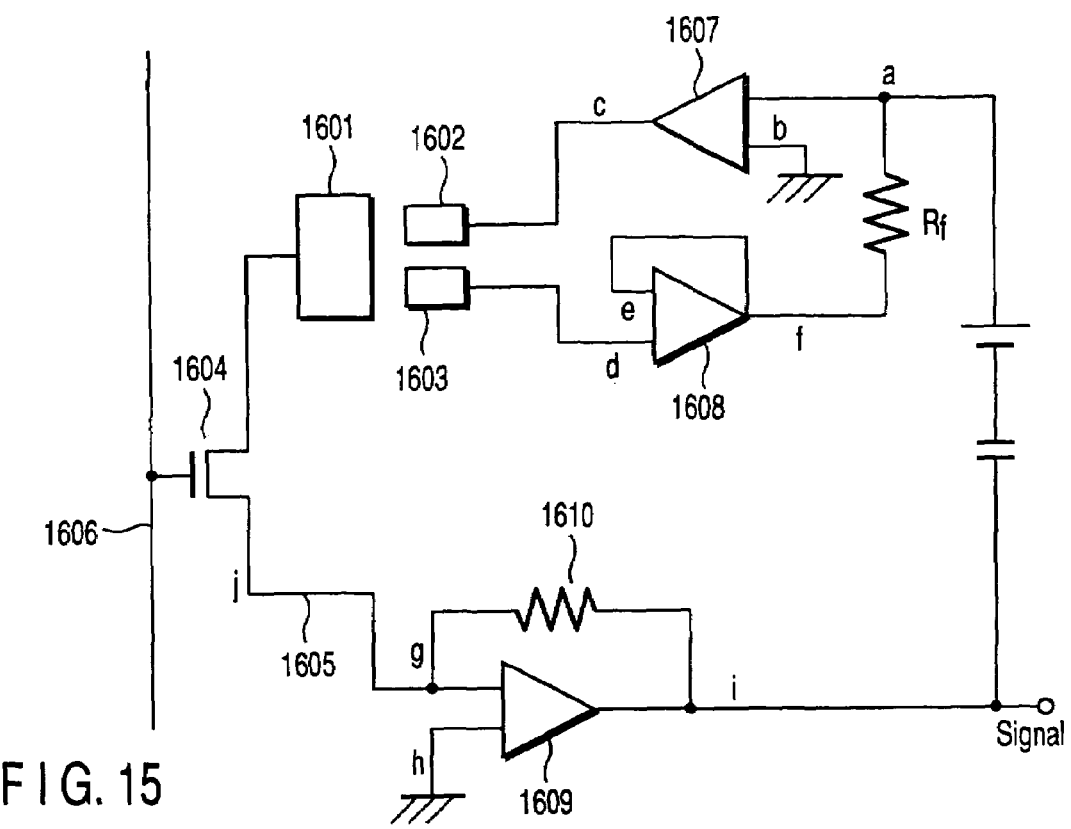
FIG. 15 is a figure, which shows an example of the circuit applied to the second nucleic acid detection chip according to the embodiment of the present invention.

The second nucleic acid detection sensor according to the present invention uses, for example, the potentiostat circuit for the minute current measurement comprising an operational amplifier 1607 which functions as a control amplifier, a voltage floor amplifier, and a current floor amplifier, an operational amplifier 1608, and an operational amplifier 1609 as shown in FIG. 15. The plurality of nucleic acid chain fixed electrodes are actually arranged to the second nucleic acid detection sensor according to the present invention though only one nucleic acid chain fixed electrode is shown in the potentiostat circuit of FIG. 15 for easiness.

This circuit comprises three operational amplifiers with the function of each control amplifier, voltage flower amplifier, and the current floor amplifier. These circuits are different from the conventional circuit in the point for the minute current measurement. Therefore, the potentiostat circuit used in the nucleic acid detection sensor may be a circuit for the minute current measurement.

The function of each operational amplifier in the circuit of FIG. 15 is as follows.

The operational amplifier 1607 configures a part of the inversion amplifier, and by applying the voltage of (1+Zf/Rf) times of ef (ef is assumed to mean the potential of point f when the common potential is assumed to be reference here, and it is same as follows) to the counter electrode 1602. ef is kept constant for ea (That is, Vcc) (Here, Zf shows electrochemical impedance from counter electrode 1602 to the reference electrode 1603). Since the operational amplifier has the negative feedback, ea is equal to eb (potential of common). In the figure, though the common is grounded, it is not unnecessary to ground.

The operational amplifier 1608 has a function to amplify an input power to Zin/Zout times (Zin and Zout are the input impedance and output impedances, respectively). Since Zin is very high compared with Zout, the output power becomes remarkably large compared with the input power. Internal resistance of the reference electrode 1603 can be disregarded by the function of the operational amplifier 1608.

Since the operational amplifier 1609 has the negative feedback, eg is equal to eh, therefore, when the nucleic acid chain fixed electrode 1601 is connected with the signal with the switching element 1604, the potential of the nucleic acid chain fixed electrode 1601 becomes equal with the potential of common. Therefore, the operational amplifier 1609 operates to keep the potential of the nucleic acid chain fixed electrode 1601 which is the action electrode to the common potential. If the ratio of the resistance (not shown in the figure) between point 0 and point a and the resistance between point a and point f is set to 1 when the input voltage is assumed to be V, the potential of the reference electrode becomes—V by the action of the operational amplifier 1603. The resistance of resistor in the circuit and the presence of the use of the resistance may be properly selected according to the desired amplification rate etc. Since the potential of the nucleic acid chain fixed electrode 1601 is equal to the potential of common; an equal voltage to the input voltage is accurately applied between the nucleic acid chain fixed electrode 1601 (action electrode) and the reference electrode 1603. The current caused by applying the voltage to the nucleic acid chain fixed electrode 1601 by the switching element 1604 connected with the scanning line 1606 from point g on signal line 1605 to point i through the resistor 1610 since the point g is grounded virtually. The largeness of the current can be measured by measuring the voltage down by the resistor 1610.

When the resistor 1610 is arranged between a point g and a point i, the error is occurred in the potential of the nucleic acid chain fixed electrode 1601 by the potential difference at both ends of the resistor. However, even if the resistor 1610 is arranged between the point g and the point i, the error is not occurred in the potential of the nucleic acid chain fixed electrode 1601 since eg is kept the potential of common. Therefore, it becomes possible to measure an electrochemical measurement of high accuracy.

Figure 16:
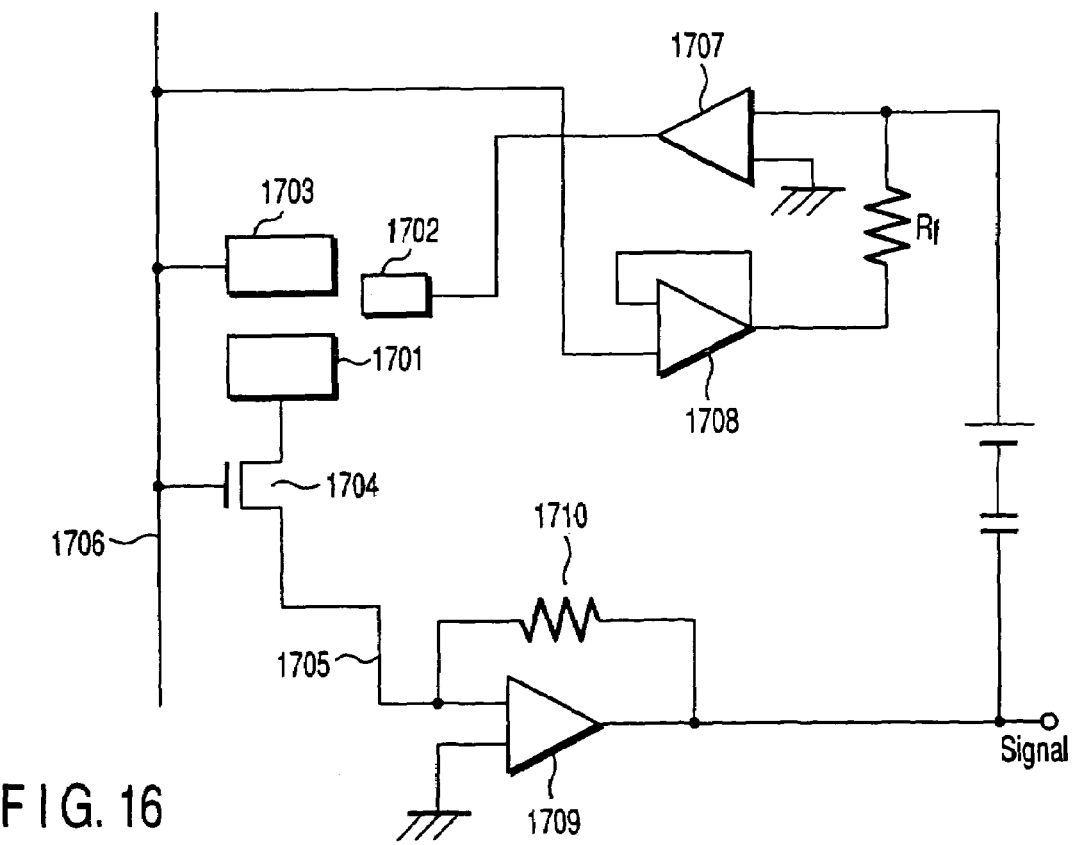
FIG. 16 is a figure, which shows another example of the circuit applied to the second nucleic acid detection chip according to the embodiment of the present invention.

The circuit of FIG. 16 is another potentiostat circuit used for the second nucleic acid detection sensor, and has a function to keep the voltage to be constant as well as the circuit of FIG. 15. Therefore, the functions of operational amplifiers 1707, 1708 and 1709 are the same as the corresponding operational amplifiers shown in FIG. 15.

Since the reference electrode is arranged to each nucleic acid chain fixed electrode as well as FIG. 15, the sensor circuit for the nucleic acid detection of this embodiment has the measurement accuracy in the sensor for compared with the conventional circuit.

Though only one reference electrode is drawn in FIG. 16 for easiness, one or more reference electrodes are arranged to each nucleic acid chain fixed electrodes, actually.

Since the reference potential is held concurrently in the circuit of FIG. 16 by the potential applied to scanning line, the wiring which is led from non-inversion input terminal of the operational amplifier 1708 is used together to the plurality of electrode, and not included in the number of wirings for the nucleic acid detection cell.

As mentioned above, the nucleic acid detection sensor of this embodiment can achieve very high measurement sensitivity with simple wiring.

Figure 17:
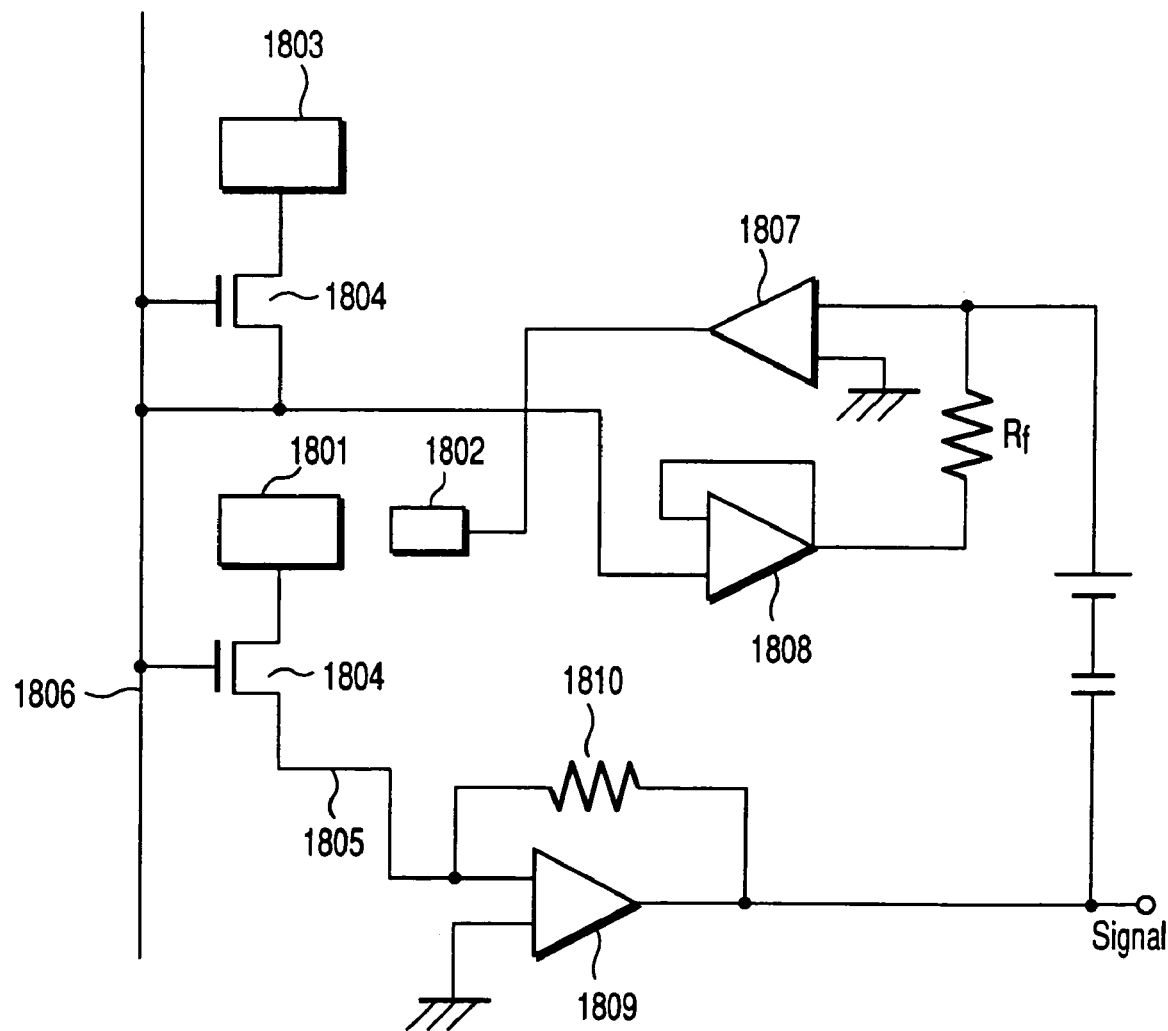
FIG. 17 is a figure, which shows another example of the circuit applied to the second nucleic acid detection chip according to the embodiment of the present invention.

The circuit of FIG. 17 is still another potentiostat circuit used for the nucleic acid detection sensor of the second embodiment, and the circuit of FIG. 17 has the function to keep the voltage to be constant as well as the circuits of FIG. 15 and FIG. 16. Therefore, details of the function of potentiostats 1807, 1808 and 1809 are as described in FIG. 15 or FIG. 16.

The circuit of FIG. 17 is different from the circuit of FIG. 16, and the reference electrode 1803 is connected with not the scanning line 1806 but the signal line 1804. Therefore, the reference electrode 1803 is not connected with the scanning line 1806 in the circuit of FIG. 17. Therefore, the reference potential of the reference electrode does not hold concurrently with the potential of the scanning line 1806, and the applied potential can be freely set. Therefore, many kinds of intorcalators can be used compared with the circuit of FIG. 16 in the circuit of FIG. 17.

The switching element may be omitted though the reference electrode 1803 is connected with switching element 1804 in FIG. 17.

The nucleic acid chain fixed electrode 1801 and the reference electrode 1803 are placed both sides of the lead which are connected with the non-inversion input terminal of the operational amplifier 1808 in FIG. 17. The reference electrode 1803 may be arranged on the same side as the nucleic acid chain fixed electrode 1801 so that two electrodes are faced.

As mentioned above, the circuit of FIG. 17 can achieve high measurement sensitivity, and can use many kinds of intorcalators.

The third nucleic acid detection sensor according to the present invention will be explained referring to FIG. 18 to FIG. 21. The third nucleic acid detection sensor according to the present invention is characterized in that the signal lines are shared by the switching element.

Figure 18:
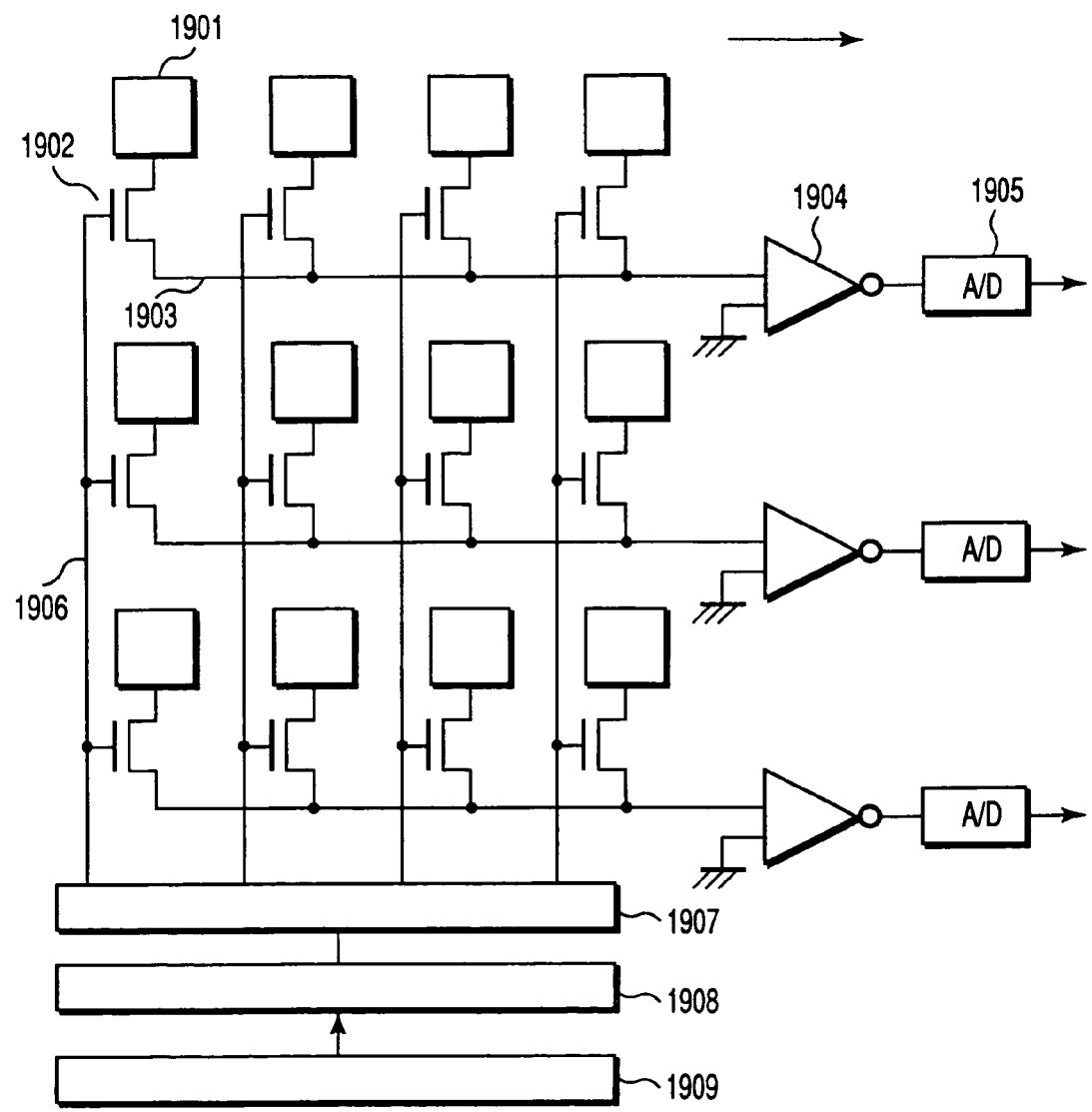
FIG. 18 is a figure, which shows the configuration of the nucleic acid detection chip according to the embodiment of the present invention in which electrodes are arranged at the opposite positions.

FIG. 18 is upper figure of the nucleic acid detection sensor which is usually used. In FIG. 18, the nucleic acid chain fixed electrodes 1901 to which the probe nucleic acid chain (not shown in the figure) is fixed are arranged in the X-Y matrix of 4×3. The counter electrode is omitted in FIG. 18, though the counter electrode is located above the plane where the nucleic acid chain fixed electrode 1901 is arranged perpendicular thereto in the sensor for actual nucleic acid detection.

Each nucleic acid chain fixed electrode 1901 forms the nucleic acid detection cell with the counter electrode.

Each nucleic acid chain fixed electrode 1901 is connected with the signal line 1903 through the switching element 1902 such as transistors. The signal line 1903 is further connected with the amplifier 1904 and the A/D converter 1905 to amplify the current from the nucleic acid chain fixed electrode 1901.

Since the clock signal is output from the timing pulse generator 1909 to the switching element 1902 through the scanning line 1906, the nucleic acid chain fixed electrodes 1901 are scanned to become active from the left end to an arrow direction in the figure one by one. The counter 1908 and the X decoder 1907 of FIG. 18 control the ON-OFF on the signal line. When the nucleic acid chain fixed electrode 1901 becomes active, the voltage is applied between the nucleic acid chain fixed electrode 1901 and the counter electrode (not shown in the figure) and the intorcalator inserted in the target nucleic acid which hybridizes with the nucleic acid chain fixed electrode 1901 is oxidized. After an electric change occurred at oxidation is amplified with said the amplifier 1904 through the signal line 1903, an electric change is A/D-converted with the A/D converter 1905.

Figure 19:
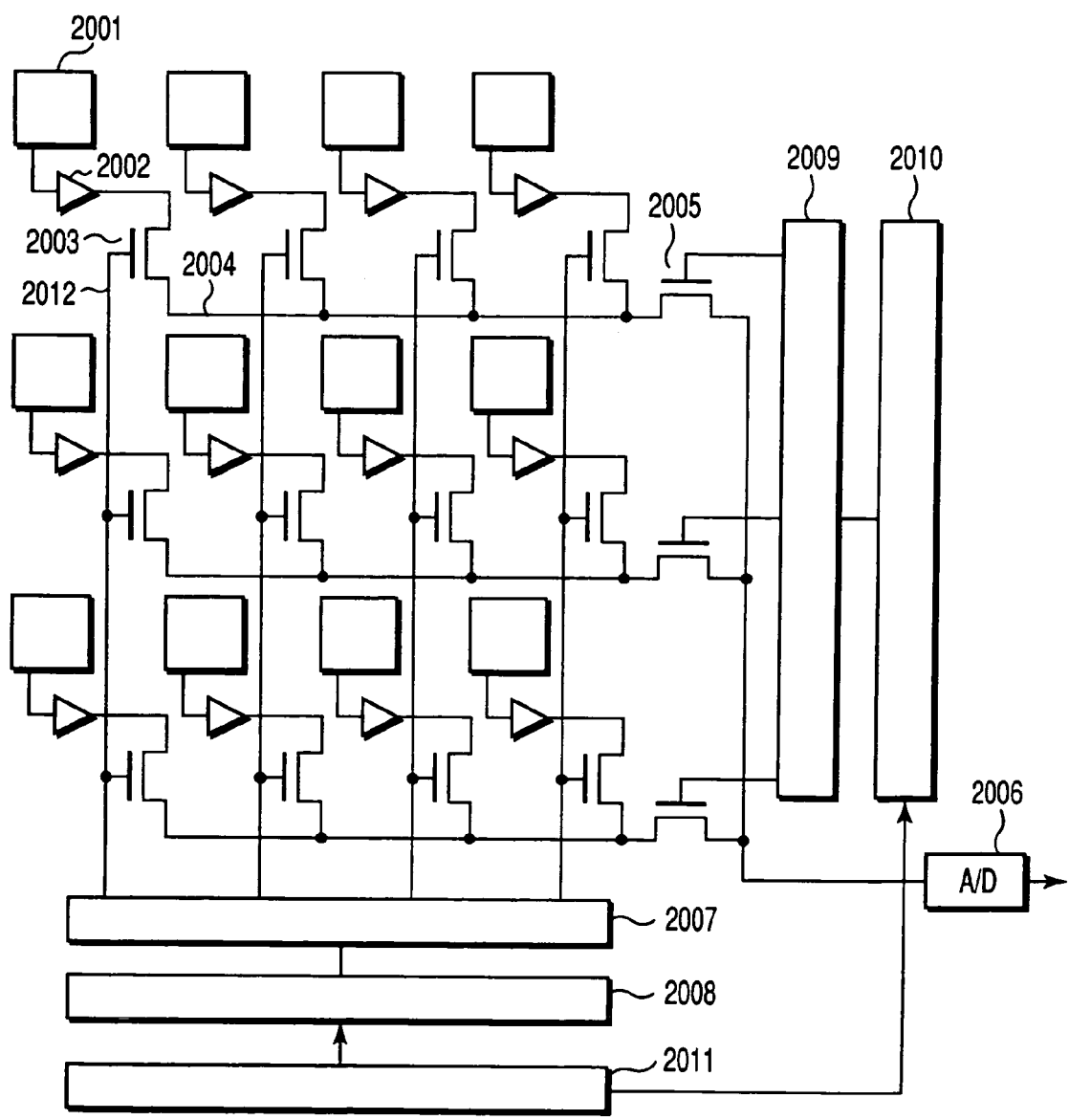
FIG. 19 is a figure, which shows a wiring in the nucleic acid detection chip according to the embodiment of the present invention in which electrodes are arranged at the opposite positions.

FIG. 19 is a figure, which shows an example of the circuit of the third nucleic acid detection sensor according to the present invention. In the nucleic acid detection sensor of FIG. 19, the point, in which the switching element is also arranged in a row direction and the scanning is performed from upper side to lower side of the FIG. 19, is different from the nucleic acid detection sensor of FIG. 18.

In FIG. 19, the nucleic acid chain fixed electrode 2001 is arranged in the X-Y matrix of 4×3, and the nucleic acid chain fixed electrode 2001 and the counter electrode (not shown in the figure) construct the nucleic acid detection cell.

Each nucleic acid chain fixed electrode 2001 is connected with the signal line 2004 through the amplifier 2002 and the electrode switching element 2003. The signal line switching element 2005 is connected with a part of each signal line 2004, and thereafter the signal lines 2004 become one line, and is connected with the A/D converter 2006.

An electric signal is output from the column direction scanning circuit, which is constructed by the X decoder 2007 and the counter 2008, to the electrode switching element 2003 one by one through the signal line 2012. On the other hand, an electric signal is output from the row direction scanning circuit, which is constructed by the Y decoder 2009 and the counter 2010 to the signal line switching element 2005 one by one.

Figure 20:
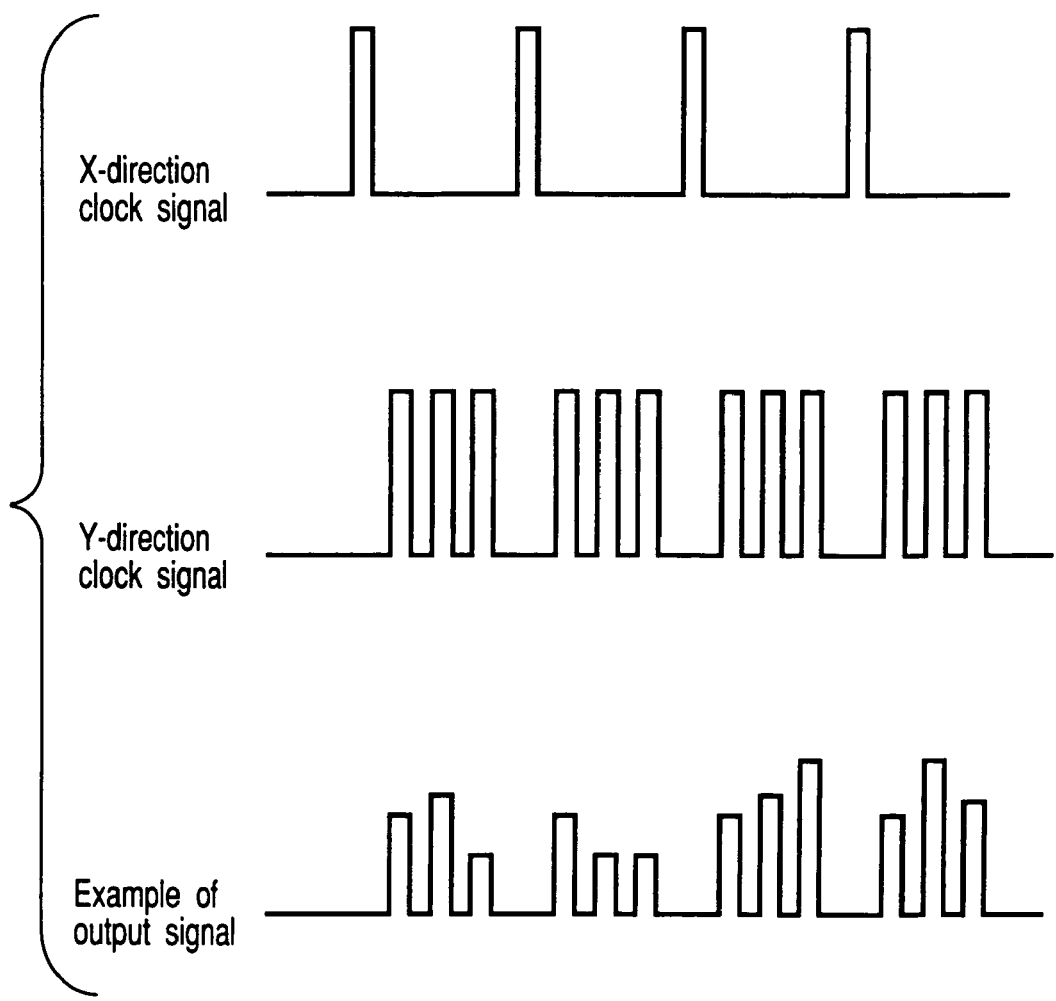
FIG. 20 is a figure, which shows the signal and the output signal to apply the voltage to each unit division.

If the clock signal generated from the timing pulse generator 2011 is output to the column direction scanning circuit and the row direction scanning circuit respectively as X direction clock signal and Y direction clock signal as shown in FIG. 20, the voltage is applied to the electrode from the first column and first row line (electrode in the top of the left), the first column and second row line, the first column and third row line, and the second column and first row line . . . one by one. An electric change, which takes place because of the application for the voltage is measured as a serial signal, and is A/D-converted into the output signal with the A/D converter.

In the nucleic acid detection sensor of FIG. 19, to detect an row direction electric signal one by one, the nucleic acid detection sensor using the scanning circuit, which is constructed by the decoder and the counter is shown. The decoder and the counter of FIG. 19 can be replaced with the shift register circuit 2210 as shown in FIG. 21. The configuration of the nucleic acid detection sensor of FIG. 21 is the same as the nucleic acid detection sensor of FIG. 19 excluding decoder and the counter being replaced with the shift register circuit. Thus, if the shift register circuit is used, the external circuit configuration becomes simple.

The third nucleic acid detection sensor shown in FIG. 19 and FIG. 21 has the effect of speeding up the measurement in compared with the nucleic acid detection sensor shown in FIG. 18.

It can be also possible to use the first to third nucleic acid detection sensors according to the present invention alone, and can be used by properly combining.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of detecting nucleic acids each having a predetermined sequence included in a test liquid, the method comprising:
    contacting the test liquid to a nucleic acid detection sensor, the nucleic acid detection sensor comprising: a plurality of nucleic acid chain fixed electrodes to each of which a probe nucleic acid chain is fixed; a counter electrode which is arranged opposite to the nucleic acid chain fixed electrodes, in which a current flows between the counter electrode and each nucleic acid chain fixed electrode; and a reference electrode, in which the reference electrode and the nucleic acid chain fixed electrodes are formed on the same plane and the reference electrode is formed so as to surround the nucleic acid chain fixed electrode;
    performing a hybridization reaction between the probe nucleic acid chains and nucleic acid chains in the test liquid; and
    measuring electrochemical signals flowing between the plurality of nucleic acid chain fixed electrodes and the counter electrode.

2. The method according to claim 1, wherein
    the counter electrode includes a plurality of counter electrodes and the plurality of counter electrodes are provided for the nucleic acid chain fixed electrodes, respectively.

3. The method according to claim 1, wherein
    the nucleic acid chain fixed electrodes and the counter electrode are arranged so that a test liquid can flow therebetween.

4. The method according to claim 1, wherein
    the measuring electrochemical signals includes detecting a current change between the nucleic acid chain fixed electrodes and the counter electrode.

5. The method according to claim 1, wherein
    a duplex chain cognitive body is added to the test liquid, and
    the measuring electrochemical signals includes detecting a current change between the nucleic acid chain fixed electrodes and the counter electrode caused by the duplex chain cognitive body.

6. The method according to claim 1, wherein
    the nucleic acid chain fixed electrodes are comb electrodes.

7. The method according to claim 1, wherein
    a plurality of reference electrodes are provided for the nucleic acid chain fixed electrodes, respectively.

8. The method according to claim 1, wherein
    the nucleic acid chain fixed electrodes and the reference electrode are comb electrodes, and the nucleic acid chain fixed electrodes and the reference electrode are arranged to be mutually engaged.

9. A method of detecting nucleic acids each having a predetermined sequence included in a test liquid, the method comprising:

contacting the test liquid to a nucleic acid detection sensor, the nucleic acid detection sensor comprising: a plurality of nucleic acid chain fixed electrodes to each of which a probe nucleic acid chain is fixed; a counter electrode, a current flowing between each of the nucleic acid chain fixed electrodes and the counter electrode; and a plurality of reference electrodes provided for the nucleic acid chain fixed electrodes, respectively, wherein the nucleic acid chain fixed electrodes are comb electrodes;

performing a hybridization reaction between the probe nucleic acid chains and nucleic acid chains in the test liquid; and measuring electrochemical signals flowing between the plurality of nucleic acid chain fixed electrodes and the counter electrode.

10. The method according to claim 9, wherein
the reference electrode is a comb electrode, and the nucleic acid chain fixed electrodes and the reference electrode are arranged to be mutually engaged.

11. The method according to claim 9, wherein
the counter electrode is comb electrode, and the nucleic acid chain fixed electrodes and the counter electrode are arranged to be mutually engaged.

12. The method according to claim 9, wherein
the measuring electrochemical signals includes detecting a current change between the nucleic acid chain fixed electrodes and the counter electrode.

13. The method according to claim 12, wherein
a duplex chain cognitive body is added to the test liquid, and
the measuring electrochemical signals includes detecting a current change between the nucleic acid chain fixed electrodes and the counter electrode caused by the duplex chain cognitive body.

14. The method according to claim 9, wherein the counter electrode includes a plurality of counter electrodes and the plurality of counter electrodes are provided for the nucleic acid chain fixed electrodes, respectively.

15. A method of detecting nucleic acids each having a predetermined sequence included in a test liquid, the method comprising:

contacting the test liquid to a nucleic acid detection sensor, the nucleic acid detection sensor comprising: a plurality of nucleic acid chain fixed electrodes to each of which a probe nucleic acid chain is fixed; a counter electrode, a current flowing between each of the nucleic acid chain fixed electrodes and the counter electrode; a plurality of reference electrodes provided for the nucleic acid chain fixed electrodes, respectively; a first amplifier which inputs a signal from the reference electrode or a scanning line; a second amplifier to input a reference potential to apply a predetermined potential to the counter electrode; and a reference resistor connected between an output side of the first amplifier and the reference potential;

performing a hybridization reaction between the probe nucleic acid chains and nucleic acid chains in the test liquid; and measuring electrochemical signals flowing between the plurality of nucleic acid chain fixed electrodes and the counter electrode.

16. The method according to claim 15, wherein
the measuring electrochemical signals includes detecting a current change between the nucleic acid chain fixed electrodes and the counter electrode.

17. The method according to claim 16, wherein
a duplex chain cognitive body is added to the test liquid, and
the measuring electrochemical signals includes detecting a current change between the nucleic acid chain fixed electrodes and the counter electrode caused by the duplex chain cognitive body.

18. The method according to claim 15, wherein
the counter electrode includes a plurality of counter electrodes and the plurality of counter electrodes are provided for the nucleic acid chain fixed electrodes, respectively.

19. A method of detecting nucleic acids each having a predetermined sequence included in a test liquid, the method comprising:

contacting the test liquid to a nucleic acid detection sensor, the nucleic acid detection sensor comprising: a plurality of nucleic acid chain fixed electrodes to each of which a probe nucleic acid chain is fixed; a counter electrode, a current flowing between each of the nucleic acid chain fixed electrodes and the counter electrode; and a plurality of reference electrodes provided for the nucleic acid chain fixed electrodes, respectively, wherein the counter electrode and the nucleic acid chain fixed electrodes are formed on the same plane and the counter electrode is formed so as to surround the nucleic acid chain fixed electrode;

performing a hybridization reaction between the probe nucleic acid chains and nucleic acid chains in the test liquid; and measuring electrochemical signals flowing between the plurality of nucleic acid chain fixed electrodes and the counter electrode.

20. The method according to claim 19, wherein
the measuring electrochemical signals includes detecting a current change between the nucleic acid chain fixed electrodes and the counter electrode.

21. The method according to claim 20, wherein
a duplex chain cognitive body is added to the test liquid, and
the measuring electrochemical signals includes detecting a current change between the nucleic acid chain fixed electrodes and the counter electrode caused by the duplex chain cognitive body.

22. The method according to claim 19, wherein
the counter electrode includes a plurality of counter electrodes and the plurality of counter electrodes are provided for the nucleic acid chain fixed electrodes, respectively.

23. A method of detecting nucleic acids each having a predetermined sequence included in a test liquid, the method comprising:

contacting the test liquid to a nucleic acid detection sensor, the nucleic acid detection sensor comprising: a plurality of nucleic acid chain fixed electrodes, to each of which a probe nucleic acid chain is fixed; at least one counter electrode; a plurality of scanning lines each configured to transmit, one by one, a select signal that selects more than one of the plurality of nucleic acid chain fixed electrodes; a plurality of signal lines configured to transmit a measurement signal from the plurality of nucleic acid chain fixed electrodes; a plurality of switching elements connected with the plurality of nucleic acid chain fixed electrodes, the plurality of scanning lines, and the plurality of signal lines, configured to turn on and turn off a connection between the plurality of nucleic acid chain fixed electrodes and the plurality of signal lines according to the select signals from the plurality of scanning lines, and provided for the nucleic acid chain fixed electrodes, respectively;

performing a hybridization reaction between the probe nucleic acid chains and nucleic acid chains in the test liquid; and measuring electrochemical signals flowing between the plurality of nucleic acid chain fixed electrodes and the counter electrode.

24. The method according to claim 23, wherein a plurality of reference electrodes are provided for the nucleic acid chain fixed electrodes, respectively.

25. The method according to claim 23, wherein the counter electrode and the nucleic acid chain fixed electrodes are formed on the same plane and the counter electrode is formed so as to surround the nucleic acid chain fixed electrode.

26. The method according to claim 23, wherein the measuring electrochemical signals includes detecting a current change between the nucleic acid chain fixed electrodes and the counter electrode.

27. The method according to claim 26, wherein a duplex chain cognitive body is added to the test liquid, and the measuring electrochemical signals includes detecting a current change between the nucleic acid chain fixed electrodes and the counter electrode caused by the duplex chain cognitive body.

28. The method according to claim 23, wherein a reference electrode is further provided.

29. The method according to claim 28, wherein the nucleic acid chain fixed electrodes and the reference electrode are comb electrodes, and the nucleic acid chain fixed electrodes and the reference electrodes are arranged to be mutually engaged.

30. The method according to claim 28, wherein the reference electrode and the nucleic acid chain fixed electrodes are formed on the same plane and the reference electrode is formed so as to surround the nucleic acid chain fixed electrode.

31. The method according to claim 23, wherein a decoder is connected to the plurality of scanning lines, and generates the select signals.

32. The method according to claim 31, wherein a timing pulse generator generates a clock signal, and a counter connects the timing generator with the decoder.

33. The method according to claim 23, wherein a plurality of A/D converters are connected to the plurality of signal lines.

34. The method according to claim 33, wherein a plurality of amplifiers are connected between the plurality of signal lines and the plurality of A/D converters.

35. The method according to claim 23, wherein a plurality of transistors are connected to the plurality of signal lines; and a common A/D converter is connected to the plurality of signal lines via the plurality of transistors.

36. The method according to claim 35, wherein a plurality of amplifiers are connected between the plurality of nucleic acid chain fixed electrodes and the plurality of transistors.

37. The method according to claim 23, wherein the plurality of signal lines are covered with insulation films.

38. The method according to claim 23, wherein the nucleic acid chain fixed electrodes are comb electrodes.

39. The method according to claim 38, wherein the counter electrode is comb electrode, and the nucleic acid chain fixed electrodes and the counter electrode are arranged to be mutually engaged.

40. The method according to claim 23, wherein
a counter electrode is provided for each nucleic acid chain fixed electrode.

41. A method of detecting nucleic acids each having a predetermined sequence included in a test liquid, the method comprising:

contacting the test liquid to a nucleic acid detection sensor, the nucleic acid detection sensor comprising: a plurality of nucleic acid chain fixed electrodes to each of which a probe nucleic acid chain is fixed; a counter electrode, a current flowing between each of the nucleic acid chain fixed electrodes and the counter electrode; and a plurality of reference electrodes provided for the nucleic acid chain fixed electrodes, respectively, wherein a reference electrode and the nucleic acid chain fixed electrodes are formed on the same plane and the reference electrode is formed so as to surround the nucleic acid chain fixed electrode;

performing a hybridization reaction between the probe nucleic acid chains and nucleic acid chains in the test liquid; and measuring electrochemical signals flowing between the plurality of nucleic acid chain fixed electrodes and the counter electrode.

42. The method according to claim 41, wherein the measuring electrochemical signals includes detecting a current change between the nucleic acid chain fixed electrodes and the counter electrode.

43. The method according to claim 42, wherein
a duplex chain cognitive body is added to the test liquid, and the measuring electrochemical signals includes detecting a current change between the nucleic acid chain fixed electrodes and the counter electrode caused by the duplex chain cognitive body.

44. The method according to claim 41, wherein the counter electrode includes a plurality of counter electrodes and the plurality of counter electrodes are provided for the nucleic acid chain fixed electrodes, respectively.

45. A method of detecting nucleic acids each having a predetermined sequence included in a test liquid, the method comprising:

contacting the test liquid to a nucleic acid detection sensor, the nucleic acid detection sensor comprising: a plurality of nucleic acid chain fixed electrodes to each of which a probe nucleic acid chain is fixed; and a counter electrode which is arranged opposite to the nucleic acid chain fixed electrodes, wherein a current flows between the counter electrode and each nucleic acid chain fixed electrode, wherein the nucleic acid chain fixed electrodes are comb electrodes;

performing a hybridization reaction between the probe nucleic acid chains and nucleic acid chains in the test liquid; and measuring electrochemical signals flowing between the plurality of nucleic acid chain fixed electrodes and the counter electrode.

46. The method according to claim 45, wherein the counter electrode is comb electrode, and the nucleic acid chain fixed electrodes and the counter electrode are arranged to be mutually engaged.

47. A method of detecting nucleic acids each having a predetermined sequence included in a test liquid, the method comprising:

contacting the test liquid to a nucleic acid detection sensor, the nucleic acid detection sensor comprising: a plurality of nucleic acid chain fixed electrodes to each of which a probe nucleic acid chain is fixed; and a counter electrode which is arranged opposite to the nucleic acid chain fixed electrodes, wherein a current flows between the counter electrode and each nucleic acid chain fixed electrode, and a reference electrode, wherein the nucleic acid chain fixed electrodes and the reference electrode are comb electrodes, and the nucleic acid chain fixed electrodes and the reference electrode are arranged to be mutually engaged;

performing a hybridization reaction between the probe nucleic acid chains and nucleic acid chains in the test liquid; and measuring electrochemical signals flowing between the plurality of nucleic acid chain fixed electrodes and the counter electrode.

* * * * *